US009877750B2

(12) United States Patent
Iott et al.

(10) Patent No.: US 9,877,750 B2
(45) Date of Patent: *Jan. 30, 2018

(54) PERCUTANEOUS VERTEBRAL STABILIZATION SYSTEM

(71) Applicant: GLOBUS MEDICAL, INC., Audubon, PA (US)

(72) Inventors: Andrew Iott, Newtown Square, PA (US); Andrew Lee, Santa Rosa, CA (US); Edward Karpowicz, Sewell, NJ (US)

(73) Assignee: Globus Medical, Inc., Audubon, PA (US)

( * ) Notice: Subject to any disclaimer, the term of this patent is extended or adjusted under 35 U.S.C. 154(b) by 10 days.

This patent is subject to a terminal disclaimer.

(21) Appl. No.: 14/987,832

(22) Filed: Jan. 5, 2016

(65) Prior Publication Data

US 2016/0135855 A1    May 19, 2016

Related U.S. Application Data

(63) Continuation of application No. 13/648,836, filed on Oct. 10, 2012, now Pat. No. 9,314,273, which is a
(Continued)

(51) Int. Cl.
*A61B 17/88* (2006.01)
*A61B 17/70* (2006.01)
*A61F 2/46* (2006.01)

(52) U.S. Cl.
CPC .......... *A61B 17/7074* (2013.01); *A61B 17/70* (2013.01); *A61B 17/7083* (2013.01);
(Continued)

(58) Field of Classification Search
CPC . A61B 17/7074; A61B 17/70; A61B 17/7083; A61B 17/7085; A61B 17/7086; A61B 17/7011; A61F 2/4611
(Continued)

(56) References Cited

U.S. PATENT DOCUMENTS

| 4,448,191 A | 5/1984 | Rodnyansky et al. |
| 5,437,667 A | 8/1995 | Papierski et al. |

(Continued)

FOREIGN PATENT DOCUMENTS

DE    10027988 A1    1/2002

OTHER PUBLICATIONS

Foley et al., "CD Horizon Sextant Rod Insertion System Surgical Technique", 28 pages, copyright 2002 (Medtronic Sofamor Danek, Inc.).
(Continued)

*Primary Examiner* — Pedro Philogene
*Assistant Examiner* — David C Comstock

(57) ABSTRACT

Systems and methods for percutaneously installing a vertebral stabilization system. A first anchor is positionable within a body of a patient through a first percutaneous opening and a second anchor is positionable within a body of a patient through a second percutaneous opening. A stabilization member is positionable within the body of a patient through the first percutaneous opening to engage and connect the first and second anchors.

18 Claims, 19 Drawing Sheets

Related U.S. Application Data continuation of application No. 12/835,118, filed on Jul. 13, 2010, now Pat. No. 8,308,728, which is a continuation of application No. 11/244,036, filed on Oct. 6, 2005, now Pat. No. 7,758,617.

(60) Provisional application No. 60/675,102, filed on Apr. 27, 2005.

(52) U.S. Cl.
CPC ...... *A61B 17/7085* (2013.01); *A61B 17/7086* (2013.01); *A61F 2/4611* (2013.01); *A61B 17/7011* (2013.01)

(58) Field of Classification Search
USPC ......... 606/279, 246, 261, 265, 266, 278, 99, 606/86 A
See application file for complete search history.

(56) References Cited

U.S. PATENT DOCUMENTS

| | | | |
|---|---|---|---|
| 5,720,751 A | 2/1998 | Jackson | |
| 5,910,141 A | 6/1999 | Morrison et al. | |
| 6,036,692 A | 3/2000 | Burel et al. | |
| 6,063,088 A | 5/2000 | Winslow | |
| 6,162,170 A | 12/2000 | Foley et al. | |
| 6,245,072 B1 | 6/2001 | Zdeblick et al. | |
| 6,440,133 B1 | 8/2002 | Beale et al. | |
| 6,530,929 B1 | 3/2003 | Justis et al. | |
| 6,610,063 B2 | 8/2003 | Kumar et al. | |
| 6,660,022 B1 | 12/2003 | Li et al. | |
| 6,790,209 B2 | 9/2004 | Beale et al. | |
| 6,821,277 B2 | 11/2004 | Teitelbaum | |
| 7,008,422 B2 | 3/2006 | Foley et al. | |
| 7,011,660 B2 | 3/2006 | Sherman et al. | |
| 7,588,588 B2* | 9/2009 | Spitler | A61B 17/1757 606/104 |
| 7,758,617 B2* | 7/2010 | Iott | A61B 17/701 606/246 |
| 8,246,624 B2 | 8/2012 | Forton et al. | |
| 9,314,273 B2* | 4/2016 | Iott | A61B 17/70 |
| 2003/0208203 A1 | 11/2003 | Lim et al. | |
| 2004/0039384 A1 | 2/2004 | Boehm, Jr. et al. | |
| 2004/0059339 A1 | 3/2004 | Roehm, III et al. | |
| 2004/0186346 A1 | 9/2004 | Smith et al. | |
| 2005/0004593 A1 | 1/2005 | Simonson | |
| 2005/0065517 A1 | 3/2005 | Chin | |
| 2005/0080418 A1 | 4/2005 | Simonson et al. | |
| 2005/0131408 A1 | 6/2005 | Sicvol et al. | |
| 2005/0131419 A1 | 6/2005 | McCord et al. | |
| 2005/0131421 A1 | 6/2005 | Anderson et al. | |
| 2005/0131422 A1 | 6/2005 | Anderson et al. | |
| 2005/0154389 A1 | 7/2005 | Selover et al. | |
| 2005/0171540 A1 | 8/2005 | Lim et al. | |
| 2005/0192589 A1 | 9/2005 | Raymond et al. | |
| 2005/0216002 A1 | 9/2005 | Simonson | |
| 2005/0234455 A1 | 10/2005 | Binder et al. | |
| 2006/0235426 A1 | 10/2006 | Lim et al. | |
| 2007/0191836 A1 | 8/2007 | Justie | |
| 2008/0077138 A1 | 3/2008 | Cohen et al. | |
| 2009/0082811 A1 | 3/2009 | Stad et al. | |

OTHER PUBLICATIONS

Foley et al., "Percutaneous pedicle screw fixationof the lumbar spine", 9 pages, Neurosurg Focus 10(4): Article 10, Apr. 2001.
"Sextant tm Percutaneous Rod Insertion System", 2 pages, copyright 2003 (Mackenzie-Spine.com).

* cited by examiner

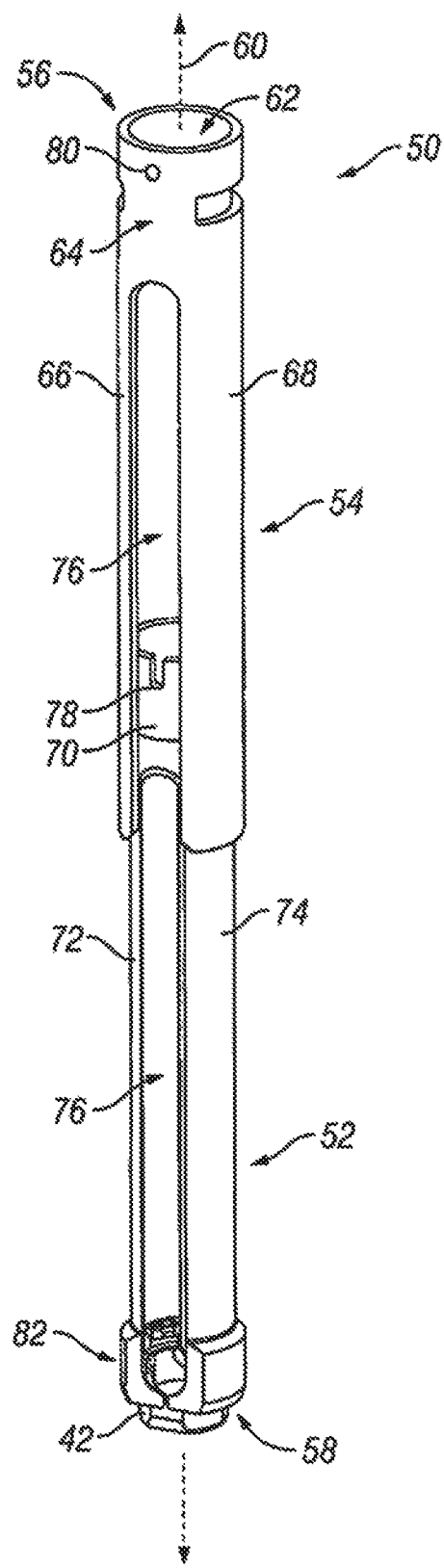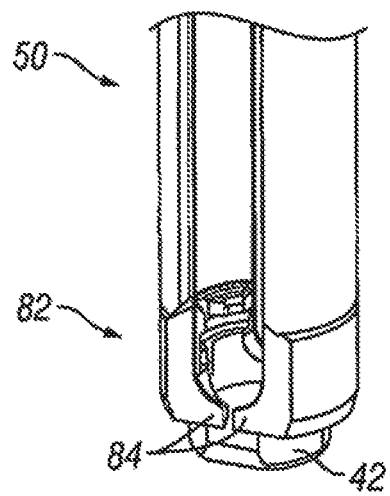
FIG. 3
FIG. 4

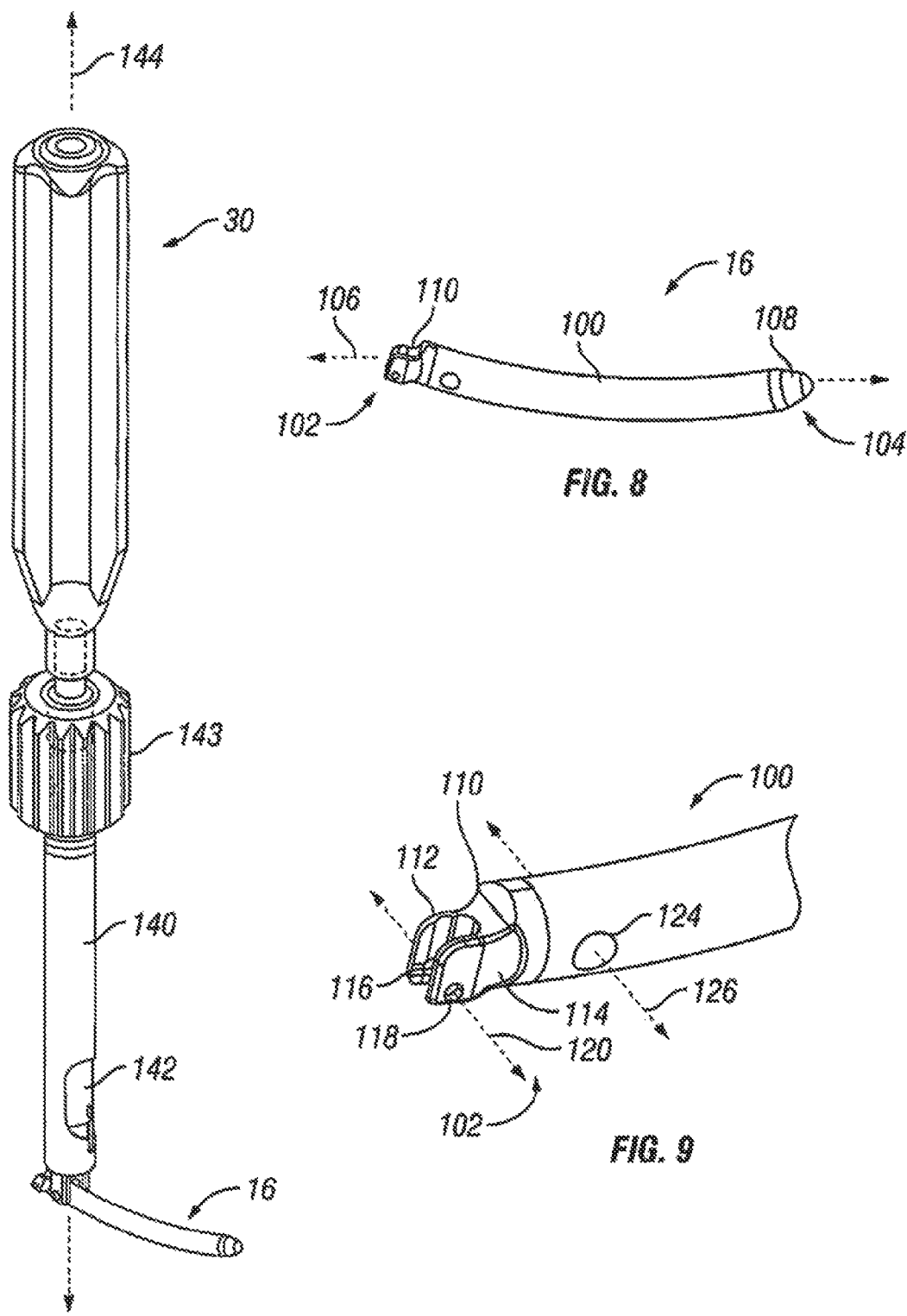

PERCUTANEOUS VERTEBRAL STABILIZATION SYSTEM

CROSS-REFERENCE TO RELATED APPLICATIONS

This application is a continuation of U.S. application Ser. No. 13/648,836, filed Oct. 10, 2012, which is a continuation of U.S. application Ser. No. 12/835,118, filed Jul. 13, 2010, now U.S. Pat. No. 8,308,728, which is a continuation of U.S. application Ser. No. 11/244,036, filed Oct. 6, 2005, now U.S. Pat. No. 7,758,617, which claims priority to U.S. Provisional Application Ser. No. 60/675,102 filed on Apr. 27, 2005, all of which are incorporated herein by reference in their entireties for all purposes.

FIELD OF THE INVENTION

The present invention relates generally to a vertebral stabilization system, and more particularly, but not exclusively, to a percutaneous vertebral stabilization system.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of screws and/or hooks to one or more vertebrae and connecting the screws or hooks to an elongate rod that generally extends in the direction of the axis of the spine.

Treatment for these spinal irregularities often involves using a system of pedicle screws and rods to attain stability between spinal segments. Instability in the spine can create stress and strain on neurological elements, such as the spinal cord and nerve roots. In order to correct this, implants of certain stiffness can be implanted to restore the correct alignment and portion of the vertebral bodies. In many cases, an anchoring member such as a pedicle screw along with a vertical solid member can help restore spinal elements to a pain free situation, or at least may help reduce pain or prevent further injury to the spine.

As the science and technology of spine surgery continues to progress, there is an increasing interest in developing alternative, minimally invasive, methods to conventional "open" spine surgery. The goals of these less invasive alternatives are to avoid the surgical exposure, dissection, and retraction of muscles and tissues that is necessary with "open" surgery. In general, a minimally invasive spine surgery system should be able to perform the same procedure as the traditional open technique, but through smaller incisions instead of one longer incision. As a result, some physicians feel that using a minimally invasive spine surgery system generally causes less soft tissue damage, reduces blood loss and reduces recovery time. In addition, patients generally prefer the smaller scars that are left using a minimally invasive approach Historically, spine fusion surgery including pedicle screw fixation with deep placement of rods has been one area that has presented significant challenges for minimally invasive approaches. However, advancement in technologies such as fluoroscopy and improvements in optics have contributed to the advent of a few minimally invasive spine fusion surgery techniques.

One example of instruments and techniques for performing surgery using minimally invasive techniques is found in U.S. Pat. No. 6,530,929 to Justis et al. The '929 patent discloses a brace installation instrument that is mounted to anchors secured in an animal subject. The installation instrument includes anchor extensions coupled to the anchors. The instrument is movable with respect to the anchors to position a brace in a position more proximate the anchors. The brace can be indexed for insertion at a predetermined orientation with respect to the installation instrument. The brace is inserted through an independent incision in the animal subject and swings along an arc that has a radius of curvature equal to the distance between the anchors and the end of the anchor extensions. While these techniques are steps in the right direction, there remains a need for instruments and methods for vertebral stabilization using minimally invasive techniques.

SUMMARY OF THE INVENTION

The present invention relates to a percutaneous vertebral stabilization system. In one aspect of the invention, a first anchor is deliverable to a vertebral body of a patient through a first percutaneous opening with an access sleeve connected thereto. The access sleeve has a central channel extending therethrough along a longitudinal axis. A stabilization member is positionable through the first percutaneous opening to engage the first anchor. A stabilization member insertion device is releasably and rotatably linked to the stabilization member and the stabilization member insertion device is configured and dimensioned to be received within the central channel such that the insertion device and the stabilization member are moveable in the longitudinal direction along the longitudinal axis to position the stabilization member adjacent the first anchor. The stabilization member is deliverable through the central channel in the access sleeve in a first orientation substantially parallel to the longitudinal axis of the access sleeve. Independent of movement along the longitudinal axis, the stabilization member is rotatably actuatable by the stabilization member insertion device to extend in a second orientation angled with respect to the first orientation to position the stabilization member in relation to the first anchor.

In another aspect of the invention, the system comprises a second anchor deliverable to a vertebral body of a patient through a second percutaneous opening with a second access sleeve connected to the second anchor. In one variation, the stabilization member insertion device is operable to place the stabilization member in a predetermined position relative to the first and second anchors.

In one embodiment, the insertion device extends from a proximal end to a distal end along a longitudinal axis, and the insertion device comprises a first member and a second member. The first member is linearly translatable with respect to the second member along the longitudinal axis. The stabilization member is linkingly engaged to the first member and rotatably engaged to the second member such that, when the first member is translated with respect to the second member along the longitudinal axis the stabilization member rotates about the second member.

In another embodiment, the first anchor comprises a coupling element connected to the access sleeve, and the coupling element comprises a portion for receiving the stabilization member. When the coupling element is connected to the access sleeve the receiving portion is unobstructed. In another aspect of the invention, each sleeve includes a pair of longitudinal openings extending along opposing lateral sides and the openings providing lateral access to the central channel. In one embodiment, the insertion device is configured to be received in the central channel and at least a portion of the stabilization member is extendable through the longitudinal openings.

In another aspect of the invention, the first and second anchors have a predetermined orientation within the body and the stabilization member has a geometry corresponding to the predetermined orientation of the first and second anchors. In one embodiment of the invention, the first and second anchors comprise polyaxial screws.

In another aspect of the invention, the stabilization member comprises a rod and in one particular embodiment of the invention the rod may have a curvilinear shape. In one embodiment, the rod has at least one indentation along its length, wherein the stabilization member insertion device is rotatably linked to the stabilization member about the indentation. In another embodiment, the rod has a proximal end configured and dimensioned to interact with the stabilization member insertion device.

The present invention also relates to a method of percutaneously installing a vertebral stabilization system. In one exemplary embodiment, a first percutaneous opening is created in a body of a patient and the method comprises positioning a first anchor to a vertebral body within the patient through the first percutaneous opening with an access sleeve connected thereto. The method further comprises, positioning a stabilization member through the first percutaneous opening to engage the first anchor. The stabilization member is rotatably linked to a stabilization member insertion device, and the stabilization member insertion device is configured and dimensioned to be received within the sleeve such that the insertion device and stabilization member are moveable in the longitudinal direction to position the stabilization member adjacent the first anchor. The method further comprises positioning the stabilization member along the longitudinal axis through the central channel in the access sleeve in a first orientation substantially parallel to the longitudinal axis of the access sleeve; and rotating the stabilization member with respect to the insertion device independent of movement along the longitudinal axis such that the stabilization member extends in a second orientation angled with respect to the first orientation to position the stabilization member in relation to the first anchor.

BRIEF DESCRIPTION OF THE DRAWINGS

The invention will be more readily understood with reference to the embodiments thereof illustrated in the attached drawing figures, in which:

FIG. 3 is a perspective view of one embodiment of a sleeve according to the present invention shown in a first position;

FIG. 4 is an enlarged partial perspective view of the sleeve of FIG. 3 shown engaging a portion of the anchor of FIG. 2;

FIG. 7 is a perspective view of one embodiment of a stabilization member insertion device according to the present invention;

FIG. 8 is a perspective view of one embodiment of a stabilization member according to the present invention;

FIG. 9 is an enlarged partial perspective view of the stabilization member of FIG. 8;

Throughout the drawing figures, it should be understood that like numerals refer to like features and structures.

DETAILED DESCRIPTION OF THE PREFERRED EMBODIMENTS

The preferred embodiments of the invention will now be described with reference to the attached drawing figures. The following detailed description of the invention is not intended to be illustrative of all embodiments. In describing preferred embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Figure 1:
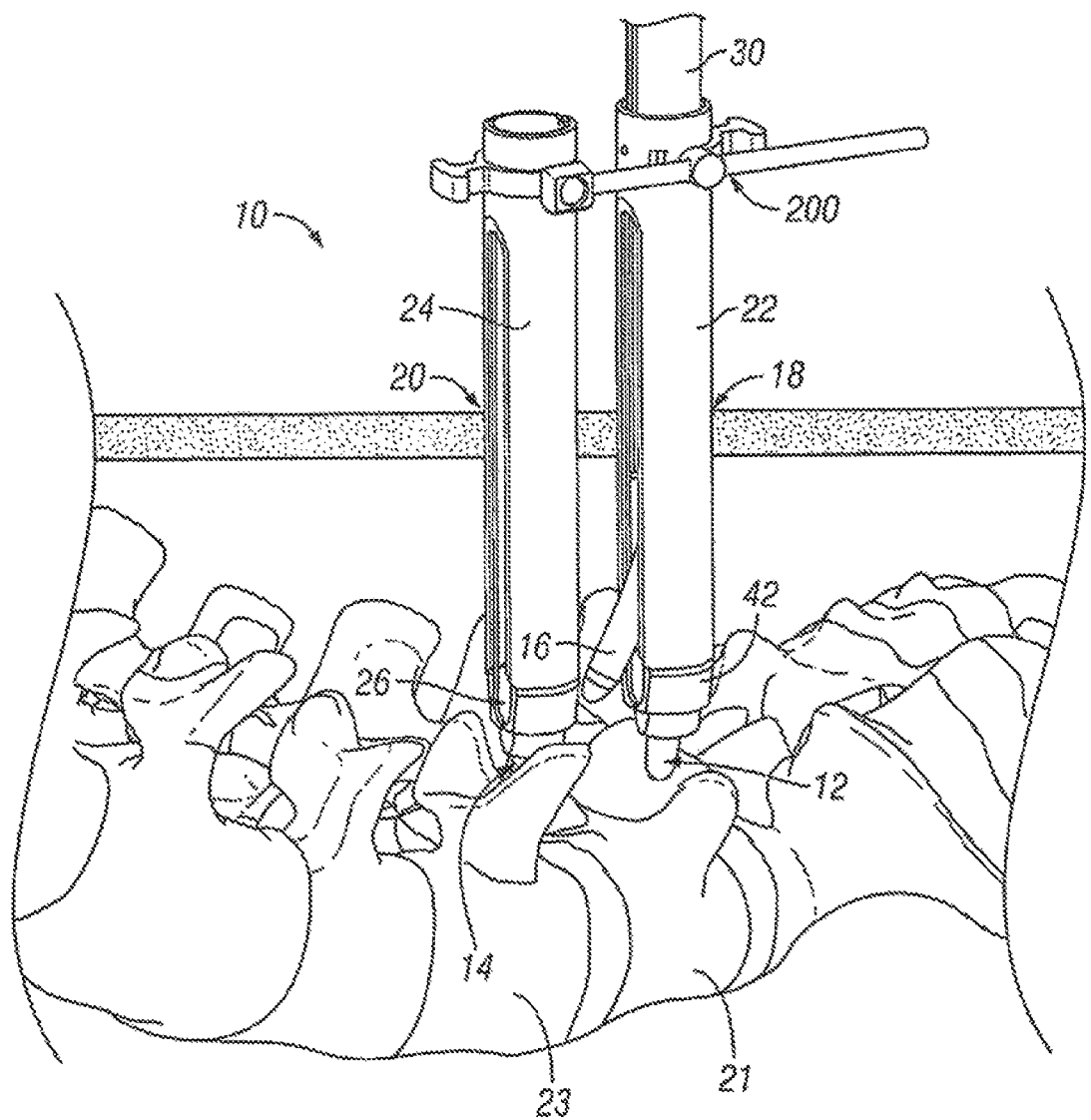
FIG. 1 is a perspective view of one embodiment of a percutaneous vertebral stabilization system according to the present invention.

Referring to FIG. 1, one embodiment of a system 10 according to the invention is shown. System 10 generally comprises a first anchor 12, a second anchor 14, and a connecting member or stabilization member 16 that is configured to connect and/or extend between the first and second anchors 12, 14 for stabilizing at least a portion of a vertebrae of a patient. First anchor 12 is positionable within a body of a patient through a first percutaneous opening 18 and a second anchor 14 is positionable within a body of a patient through a second percutaneous opening 20. In one embodiment, first and second anchors 12, 14 are configured to engage first and second vertebra 21, 23. Stabilization member 16 is positionable within the body of a patient through first percutaneous opening 18 to engage and connect first and second anchors 12, 14. Sleeves 22, 24 extend from anchors 12, 14 and facilitate insertion of anchors 12, 14 and stabilization member 16 and fixation of stabilization member 16 to anchors 12, 14. Stabilization member 16 may be installed percutaneously or non-percutaneously into receiving portions or channels 26 of anchors 12, 14. Connecting member or stabilization member 16 generally comprises an elongate rod or shaft. Stabilization member 16 may have an arcuate or curvilinear shape. In alternative embodiments, however, stabilization member 16 can include any configuration known for a rod, implant, or fastener, and can be straight or have any curvature along its length including a compound curvature. As shown in FIG. 1, a stabilization member insertion device 30 may be inserted into sleeve 22 to facilitate insertion of stabilization member 16 into anchors 12, 14.

In one embodiment, stabilization member insertion device 30 is releasably and rotatably linked to the stabilization member 16 and the stabilization member insertion device 30 is configured and dimensioned to be received within the sleeves 22, 24 such that the insertion device 30 and stabilization member 16 are moveable in the longitudinal direction within the sleeve to position stabilization member 16 adjacent the anchors 12, 14. As will be discussed in more detail below, stabilization member 16 is deliverable through the sleeve in a first orientation substantially parallel to the axis of the sleeve and is rotatable to a second orientation at an angle with respect to the first orientation. Furthermore, the stabilization member 16 is rotatably actuatable by insertion device 30 independent of movement along the axis of the sleeve, i.e. the stabilization member 16 may be rotated by insertion device 30 anywhere along the length of the sleeves 22, 24. Such a feature may be particularly advantageous, for example, to adjust the pathway or route that the stabilization member 16 travels through the body tissue during installation. In addition, due to the independent aspect of the rotation of the stabilization member, rotation may be actuated or independently controlled without moving the insertion device with respect to the sleeves 22, 24. In this regard, rotation of stabilization member 16 may be rotated without downward exertion of force upon the sleeve and/or anchor.

Figure 2:
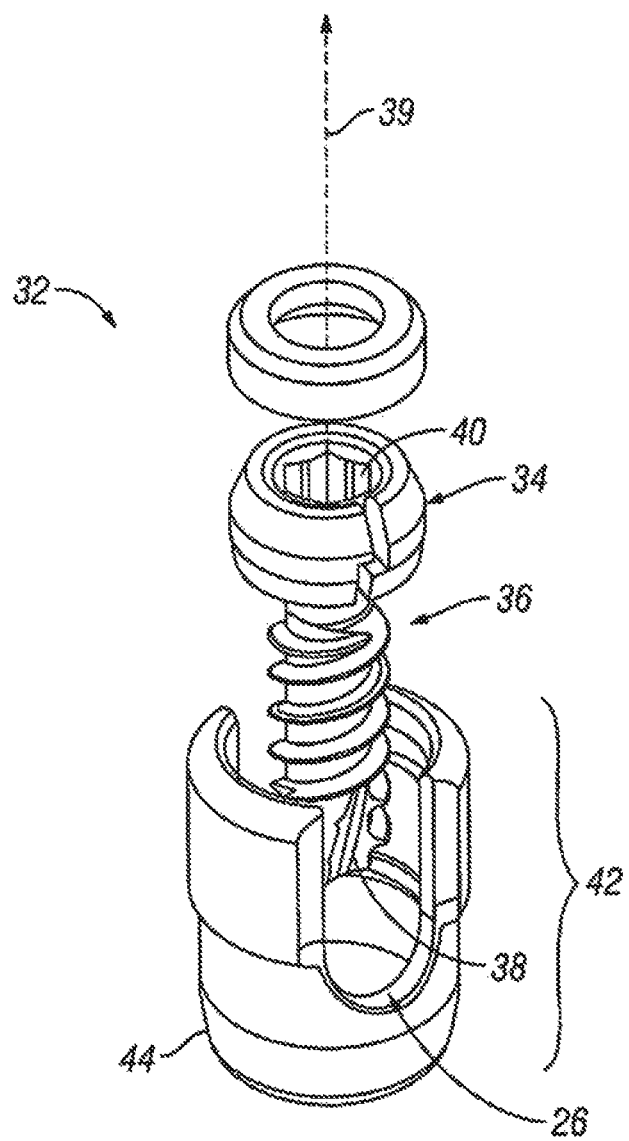
FIG. 2 is an expanded view of one embodiment of an anchor according to the present invention.

Each of the first and second anchors 12, 14 generally comprises a bone fastener such as a bone screw 32 with a head 34 and a shaft or shank 36 having bone engaging threads. As shown in FIG. 2, screw 32 is cannulated with a central passage or lumen 38 extending along a central axis 39, however, non-cannulated screws may also be used. Head 34 includes a tool engagement surface or opening 40 configured to receive a driving tool to provide torque and drive the screw into bone. In one embodiment, screw 32 is a polyaxial screw assembly that has a coupling element 42 pivotably coupled to head 34 of screw 32. In this regard, screw 32 is capable of rotating within coupling element 42 to assume a plurality of angles. One example of a polyaxial screw that may be used with the present invention is described in co-pending U.S. patent application Ser. No. 10/826,285, the entire contents of which are incorporated by reference.

Referring to the embodiment of FIG. 2, coupling element 42 is configured and adapted to receive the stabilization member 16. In general, coupling element 42 includes a U-shaped body 44 defining a channel 26 in which stabilization member 16 may be locked or fixed in place by, for example, a locking cap. In alternate embodiments, alternative means of rigidly coupling stabilization member 16 to an anchor may be used by those skilled in the art, including alternative configurations of coupling elements and locking devices or methods. In one embodiment, coupling element 42 includes features to couple with sleeves 22, 24.

In the illustrated embodiment, sleeves 22, 24 may extend from each of the anchors 12, 14 and provide a portal or passageway through the body of a patient to access anchors 12, 14. Referring to FIGS. 3-6, one embodiment of a sleeve 50 according to the invention is shown comprising an inner sleeve member 52 and an outer sleeve member 54 extending from a proximal end 56 to a distal end 58 along an axis 60. Inner sleeve member 52 and outer sleeve member 54 have a central channel 62 extending axially through sleeve 50 and the sleeve members 52, 54 are axially slidable with respect to each other. Outer sleeve member 54 generally comprises an extended tube with a generally cylindrical top portion 64 and a pair of generally rigid arms 66, 68 extending axially from top portion 64 in a distal direction. Inner sleeve member 52 generally comprises an extended tube with a generally cylindrical top portion 70 and a pair of semi-cylindrical flexible arms 72, 74 extending axially from top portion 70 in a distal direction. Slots or openings 76 extend along the lateral sides of sleeve 50 to provide access to central channel 62 of sleeve 50. Openings 76 extend axially between the arms of the inner and outer sleeve members from the top portion to the distal end of the sleeve members. According to one embodiment, a slot 78 may be provided adjacent the proximal end of top portion 64 of inner sleeve member 52 to engage a pin 80 extending radially inward from the top portion 70 of outer sleeve member 54 to orient the sleeve members 52, 54 together and align the openings 76 between the inner and outer sleeve members. Sleeve 50 may be made of any material suitable for surgical instruments. In one preferred embodiment, sleeve 50 may be made of a metal material.

In operation, arms 72, 74 of inner sleeve member 52 may be compressed radially inward or expanded radially outward depending on the particular application. Inner sleeve member 52 also includes a retainer portion 82 at its distal end to attach an anchor to the distal end of sleeve 50. As best seen in FIG. 4, arms 72, 74 may include finger members 84 extending laterally inward from the distal end to provide additional retention capability.

Figure 5:
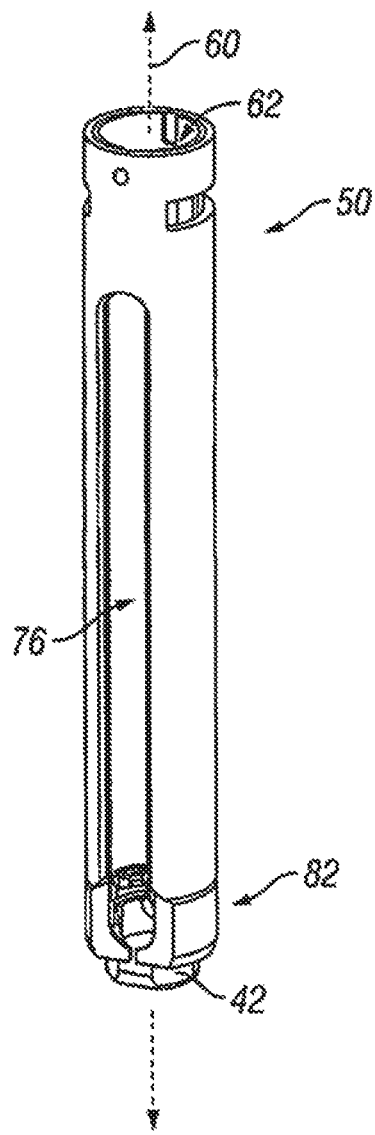
FIG. 5 is a perspective view of the sleeve of FIG. 3 shown in a second position.
Figure 6:
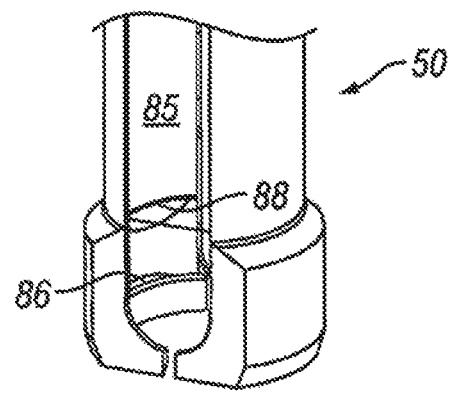
FIG. 6 is an enlarged partial perspective view of the sleeve of FIG. 3 shown without an anchor retained therein.

In FIGS. 3-5, sleeve 50 is shown with coupling element 42 of bone screw 32 is received within retainer portion 82 at a distal end 58 of inner sleeve member 52 of sleeve 50. In one variation, bone screw 32 may be inserted into inner sleeve member 52 from the bottom or distal end 58 when the inner sleeve member 52 is extended axially outside of the outer sleeve member (the position shown in FIG. 3). In this regard, retainer portion 82 may snappably or resiliently receive the coupling element 42 of screw 32. The inner wall 85 of retainer portion 82 is shaped to conform to the outer perimeter of coupling element 42 such that when arms 72, 74 of inner sleeve member 52 are compressed radially inward, the coupling element 42 of screw 32 is rotationally and axially fixed with respect to sleeve 50 or radially contained within sleeve 50. As shown in FIG. 6, in one embodiment, the inner wall 85 of retainer portion 82 includes a bottom ridge wall 86 and an upper ridge wall 88. Bottom ridge wall 86 is configured and adapted to engage the underside of coupling element 42 of screw 32 and upper ridge wall 88 is configured and adapted to engage the top of coupling element 42 to axially fix screw 32 with respect to sleeve 50. When outer sleeve member 54 is slid down over inner sleeve member 52, inner sleeve member 52 compresses against or radially contains coupling element 42 to hold it firmly against the inner wall 85 of retainer portion 82. Furthermore, finger members 84 provide additional retention capability along the lateral sides of coupling element 42. In this regard, anchors 12, 14 may be mounted to sleeve 50 and held in a fixed position relative to sleeve 50 and axis 60 of sleeve 50 is aligned with axis 39 of bone screw 32 such that when a guidewire, or a tool is inserted into screw 32, screw 32 and sleeve 50 are maintained in this aligned position. Furthermore, when the coupling element is attached to sleeve 50, the channel 26 or portion for receiving the stabilization member is unobstructed such that the stabilization member or rod may be unimpeded by, for example, a shelf, guide, ramp, or any other protrusion extending inward from the sleeve interior, during insertion into channel 26. In addition, installation of the stabilization member into channel 26 is simplified without having to remove such an obstruction prior to inserting the stabilization member into channel 26.

Figure 18:
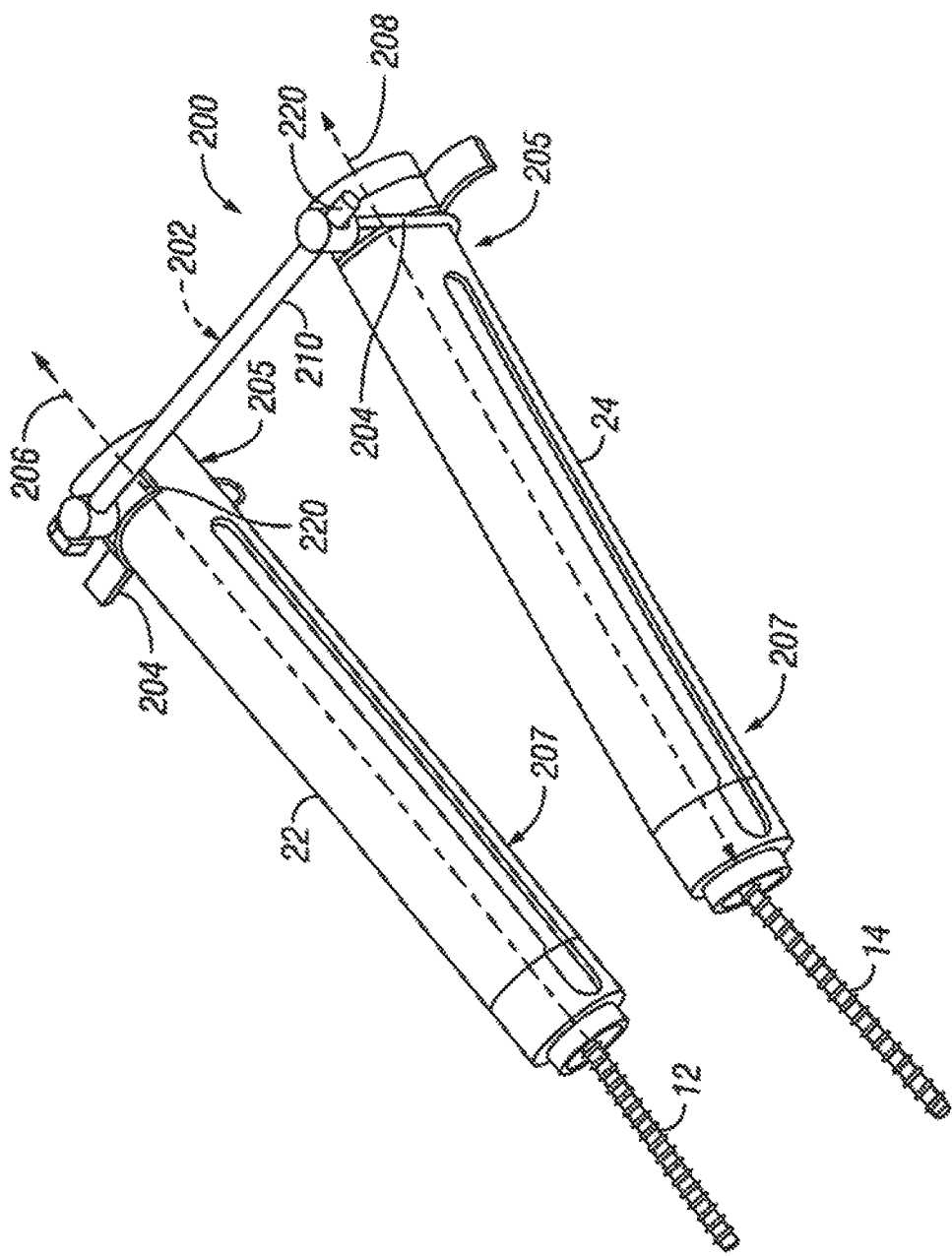
FIG. 18 is a perspective view of one embodiment of an alignment device according to the present invention.
Figure 19:
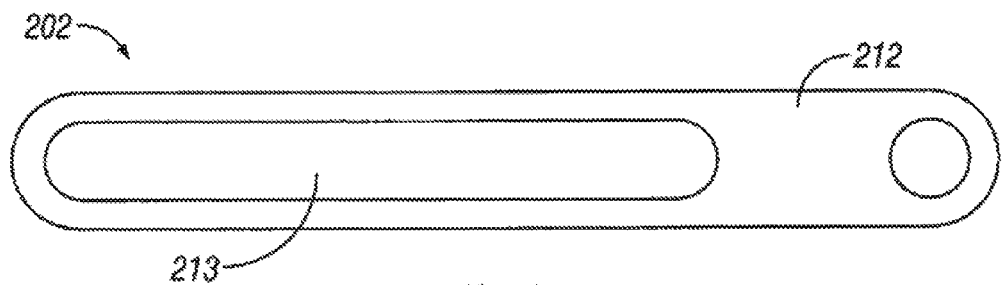
FIG. 19 is a side view of one embodiment of a sleeve attachment member according to the present invention.

Referring now to FIG. 18, one embodiment of an alignment tool 200 is shown that may be used with system 10 of FIG. 1. Alignment tool 200 generally comprises a connecting element 202 extending between sleeve attachment members 204. Sleeve attachment members 204 are configured and dimensioned to attach to the proximal end 205 of sleeves 22, 24. In one variation, connecting element 202 may have a cylindrical cross-section. In other embodiments, connecting element 202 may have a polygonal or multisided cross-section. In the embodiment of FIG. 18, the connecting element 202 is shown extending along a lateral side of sleeves 22, 24, however, in alternate embodiments, connecting element 202 may be placed or located on either side, or both sides, of the sleeves 22, 24. Connecting element 202 is configured to connect to sleeve attachment members 204 to constrain or align sleeve 22, 24 in a common plane. For example, as shown in FIG. 18, the longitudinal axis 206 of sleeve 22 is coplanar with axis 208 of sleeve 24 when alignment tool 200 is attached to system 10. By extension, the channels of anchors 12, 14 are aligned such that when stabilization member 16 is inserted, it may reliably align and extend from first anchor 12 to second anchor 14. In one embodiment, shown in FIG. 18, the connecting element 202 comprises a longitudinal rod 210. Referring to FIG. 19, another embodiment of connecting element 202 is shown and element 202 comprises a bar or plate 212 having a slot 213. In alternate embodiments, connecting element 202 may have any alternate shape known to those skilled in the art such that the axes 206, 208 of sleeves 22, 24 to which it is connected are coplanar when alignment tool 200 is attached.

Figure 20:
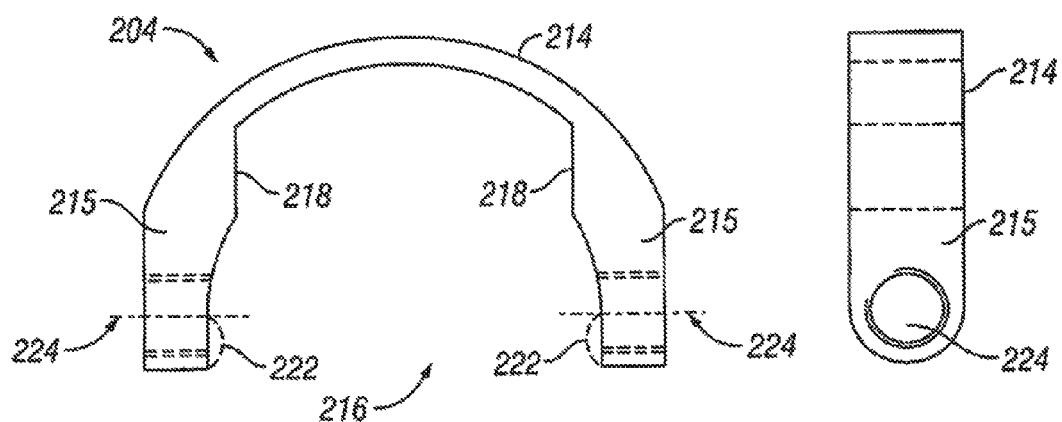
FIG. 20 is a side view of another embodiment of a connecting element according to the present invention.
Figure 21:
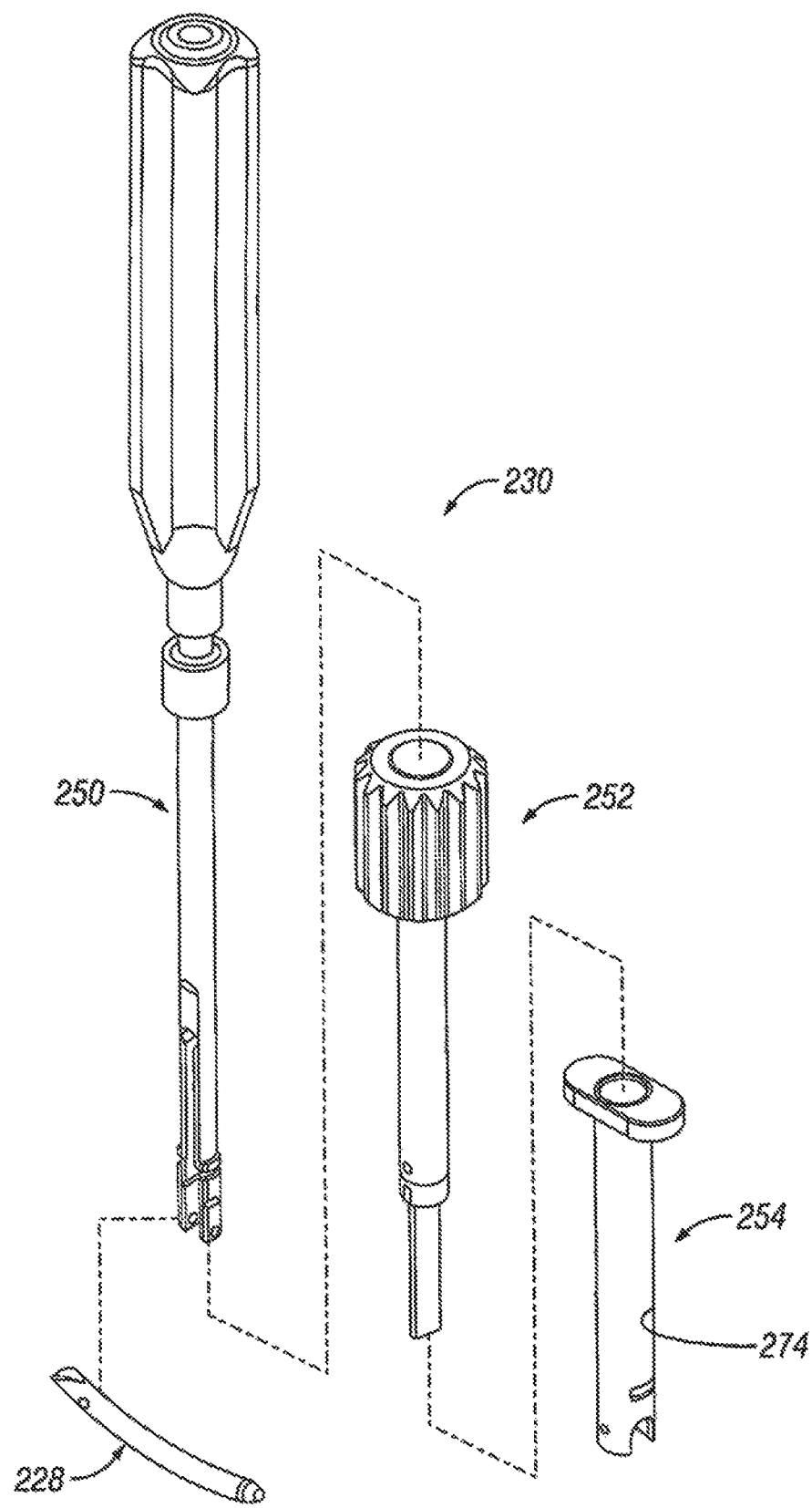
FIG. 21 is an exploded view of another embodiment of a stabilization member insertion device according to the present invention.

Referring to FIG. 20, in one embodiment sleeve attachment member 204 may comprise a C-shaped clip 214. Clip 214 generally comprises arms 215 defining an open end 216 configured and dimensioned to engage and attach to the proximal ends 205 of sleeves 22, 24. In this regard, clip 214 may comprises parallel flat surfaces 218 on the inner surface thereof to engage, register, and/or align with openings 220 of sleeves 22, 24 to maintain the sleeves 22, 24 in a fixed position with respect to clip 214. In one variation, clip 214 may include protrusions 222 extending radially inward from the inner surface such that clip 214 may snappedly engage sleeves 22, 24. Threaded mounting holes 224, extend through the arms 215 of clip 214 to mount the connecting element 202 thereto. For example, in the slotted bar embodiment shown in FIG. 19, a set screw 226 may be used to attach the slotted plate 212 to clip 214. Also, once sleeves 22, 24 are aligned with the alignment tool 200, there is still flexibility to move sleeves 22, 24 with respect to each other and as a unit. Once attached, slotted plate 212 may be adjusted along the slot 213 to move the proximal ends 205 of sleeves 22, 24 closer together or further apart, as desired. Similarly, in the rod shaped connecting element shown in FIG. 18, the proximal ends 205 of sleeves 22, 24 may be moved along the rod 210. Furthermore, once alignment tool 200 is attached to system 10 the sleeves 22, 24 may be moved together as a unit angularly about the distal ends 207, while maintaining coplanar relationship of axes 206, 208 and alignment of channels 26 of the anchors 12, 14.

Figure 9A:
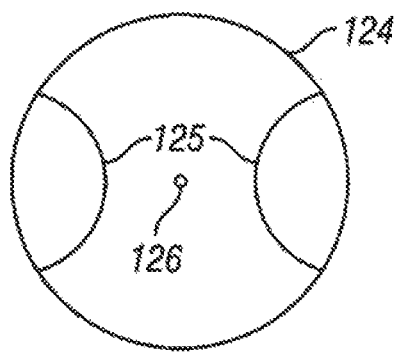
FIGS. 9A-9C are enlarged side views of alternative indentations of the stabilization member of FIG. 9.
Figure 9B:
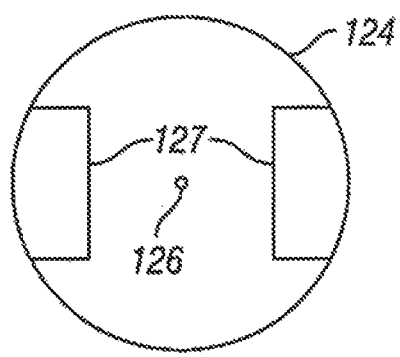
Figure 9C:
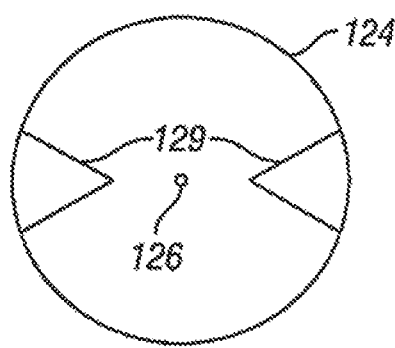

Referring now to FIGS. 7-12, one embodiment of a stabilization member 16 and insertion device 30 is shown. As shown in FIGS. 8 and 9, stabilization member 16 generally comprises an elongate rod 100 extending from a proximal end 102 to a distal end 104 along an axis 106. In one embodiment, rod 100 is curved or arcuate along its length. However, in alternate embodiments, rod 100 may have any alternate shape. According to one aspect of the embodiment, rod 100 includes a generally tapered or conical shaped nose or tip 108 at its distal end 104 to facilitate insertion and installation of rod 100 into the body of a patient. In alternate embodiments, tip 108 may have varied shapes and sizes.

A linkage connector 110 is provide at the proximal end 102 of rod 100 and comprises a pair of generally flat arm members 112, 114 extending proximally from proximal end 102 of rod 100. Holes 116, 118 extend through each arm member 112, 114, respectively and are coaxially positioned along a linkage axis 120. Holes 116, 118 are configured and dimensioned to linkingly engage a driving link arm 132 of insertion device 30. In one embodiment, rod 100 is removably linked to arm 132 such that rod 100 may be detached from arm 132 as desired by an operator of insertion device 30. In another embodiment, ball detents 134 protrude outward from arm 132 to engage holes 116, 118. In this regard, slots 122 may be provided adjacent holes 116, 118 to facilitate insertion and removal of ball detents from holes 116, 118.

Referring again to FIG. 8, in one embodiment, rod 100 may include a pair of diametrically opposed indentations 124 spaced from proximal end 102 of rod 100. Indentations 124 are coaxially aligned on a pivot axis 126 that extends generally perpendicular to a central axial plane of rod 100 and pivot axis 126 generally defines an axis about which rod 100 may pivot. Indentations 124 are configured and dimensioned to releasably rotatably engage pivot arms 136, 137 of insertion device 30 such that rod 100 may pivot with respect to pivot arms 136, 137. In a preferred embodiment, indentations 124 comprise semispherical concave shapes that cooperatively engage semispherical protrusions 138 extending from pivot arms 136, 137. In alternative embodiments, shown in FIGS. 9A-9C, indentations 124 may comprise alternative shapes when viewed along axis 126 such as a pair of laterally spaced semi-circular indentations 125 shown in FIG. 9A, a pair of laterally spaced rectangular indentations 127 shown in FIG. 9B, or a pair of laterally spaced triangular indentions 129 shown in FIG. 9C. To attach rod 100 to pivot arms 136, 137, the pivot arms may be resiliently expanded slightly to allow protrusions 138 engage or snap into indentations 124. In operation, once protrusions 138 cooperatively engage indentations 124, rod 100 may rotate or pivot about pivot axis 126.

Figure 10:
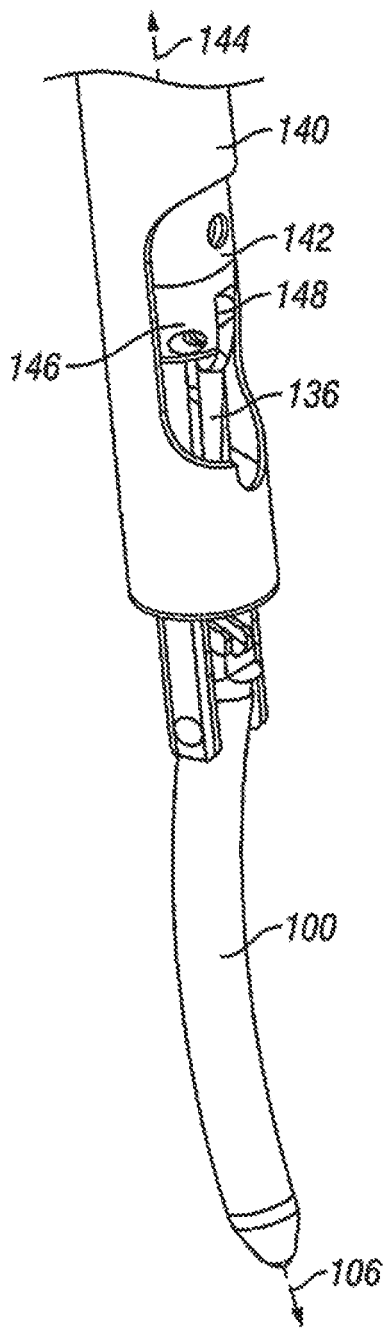
FIG. 10 is an enlarged partial perspective view of the insertion device of FIG. 7 shown in a first position.
Figure 11:
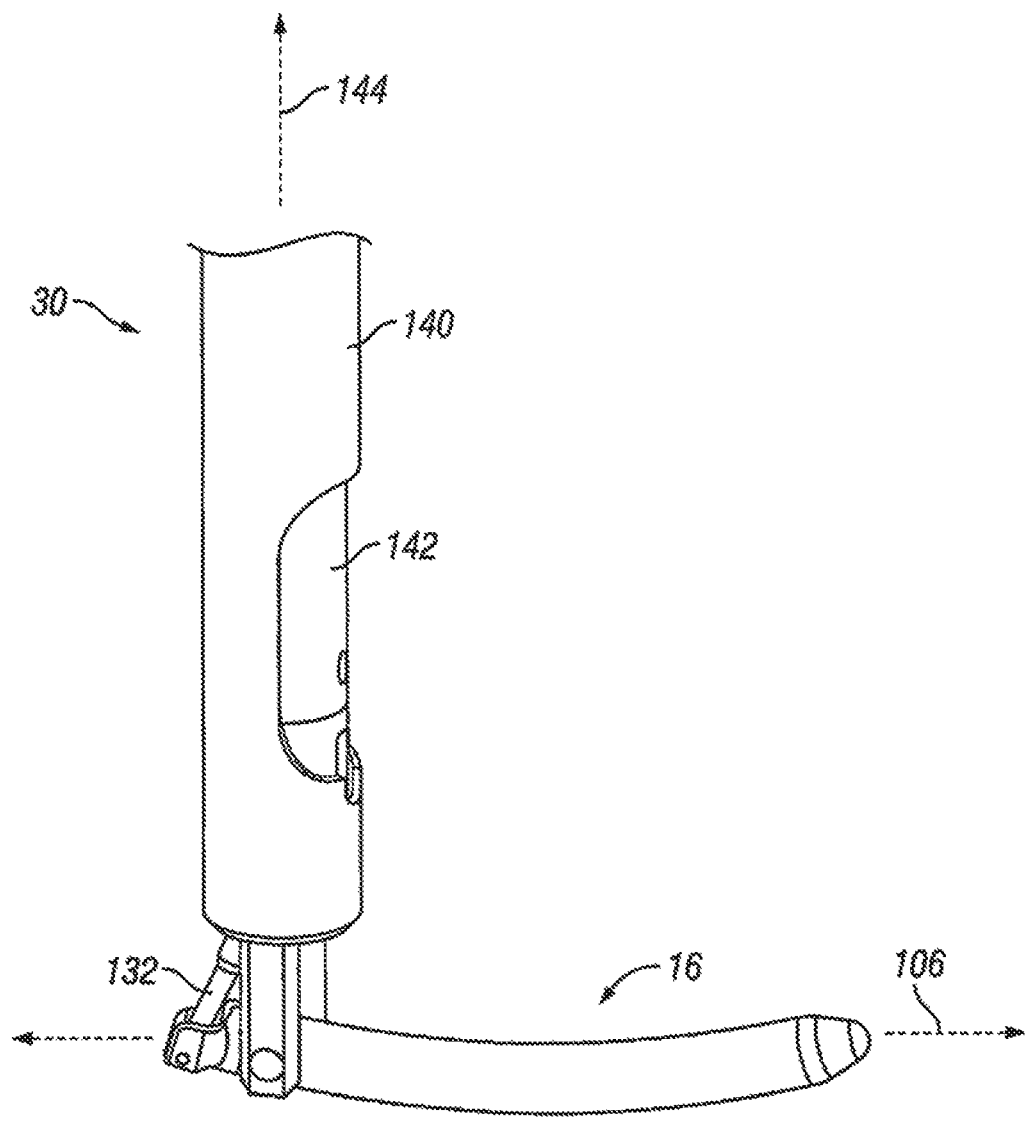
FIG. 11 is an enlarged partial perspective view of the insertion device of FIG. 7 shown in a second position.
Figure 12:
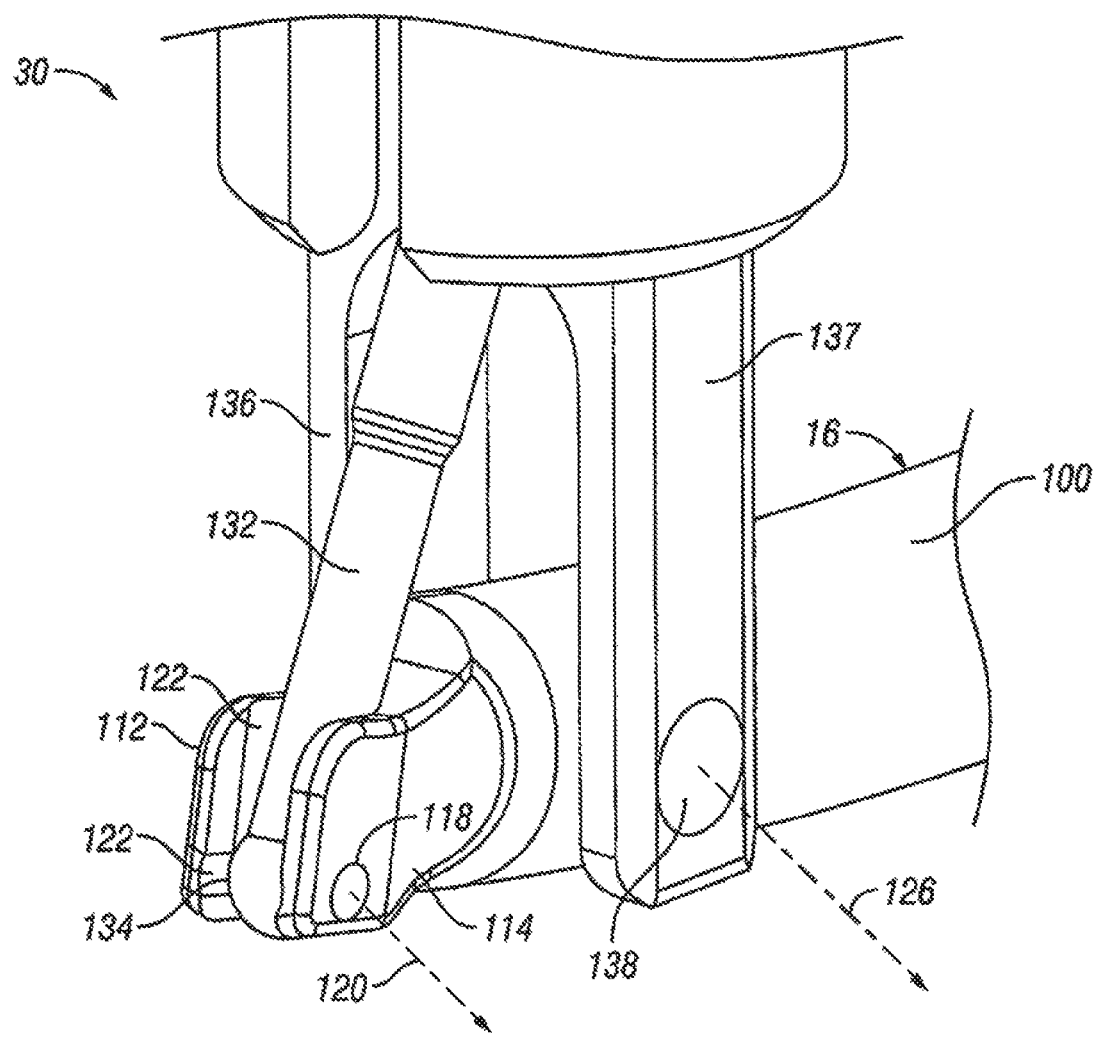
FIG. 12 is another enlarged partial perspective view of the insertion device of FIG. 7 shown in a first position.

Referring to FIGS. 7 and 10-12, stabilization member insertion device 30 generally comprises an outer tube 140 and an inner shaft 142 concentrically disposed within outer tube 140. Inner shaft 142 is moveable with respect to outer tube 140 along a longitudinal axis 144. Knob 143 is internally threaded to mate with external threads of inner shaft 142 such that rotation of knob 143 causes linear translation of inner shaft 142 with respect to outer tube 140 along axis 144. End member 146 is rotatably linked to the distal end of inner shaft 142 and is rotatably linked to the proximal end 148 of a driving link arm 136 about an axis 150. The distal end of driving link arm 136 is rotatably linked to the proximal end 102 of rod 100. A pair of pivot arms 136, 137 extend distally from the outer tube 140 and releasably linked to rod 100 at pivot axis 126. In operation, when shaft 142 is moved downward or in the distal direction along axis 144 with respect to outer tube 140, driving link arm 136 pushes or drives the proximal end 102 of rod 100 downward or in the distal direction and causes rod 100 to rotate or pivot about pivot axis 126. Thus, rod 100 is moveable from a generally upright orientation or position or a position wherein axis 144 is aligned with or parallel to axis 106 (FIG. 10) to a more horizontal orientation or position or a position wherein axis 144 is perpendicular or angled with respect to axis 106 (FIG. 11). As described above, in one embodiment stabilization member 16 is rotatably actuatable by insertion device 30 independent of movement along the axis of the sleeve, i.e. the stabilization member 16 may be rotated by insertion device 30 anywhere along the length of the sleeves 22, 24.

Figure 22:
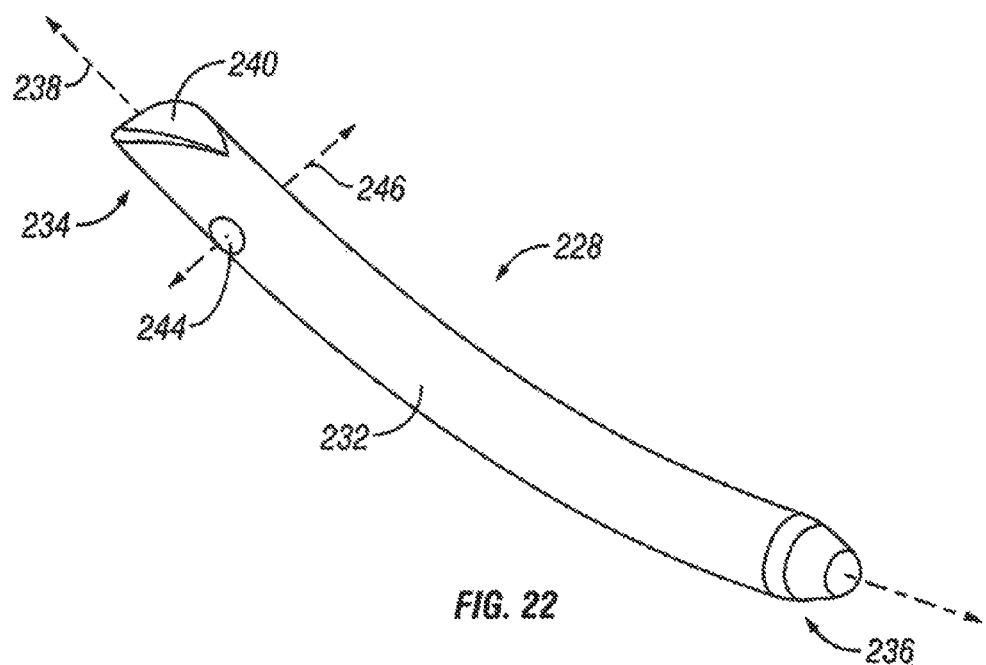
FIGS. 22-23 are perspective views of another embodiment of a stabilization member according to the present invention.
Figure 23:
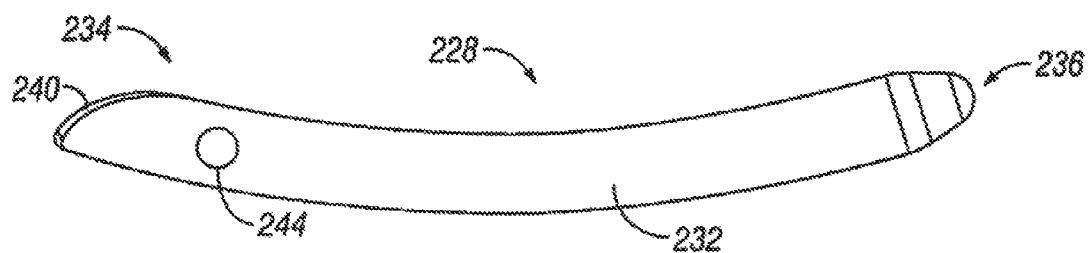

Referring now to FIGS. 21-28, another embodiment of a stabilization member 228 and insertion device 230 is shown. As shown in FIGS. 22 and 23, stabilization member 228 generally comprises an elongate rod 232 extending from a proximal end 234 to a distal end 236 along an axis 238. Rod 232 is similar to rod 100 in many respects, however, proximal end 234 differs from proximal end 102 of rod 100. Proximal end 234 of rod 232 comprises a generally concave or rounded ramped tip surface 240 angled with respect to longitudinal axis 238 configured and dimensioned to interface or engage with an actuating or pushing member 242 of insertion device 230. Rod 232, like rod 100 described above, includes diametrically opposed indentions 244 that function similar to indentations 124 described above such that rod 232 may rotate about a pivot axis 246 extending between indentations 244 when rod 232 is connected to insertion device 230.

Figure 24:
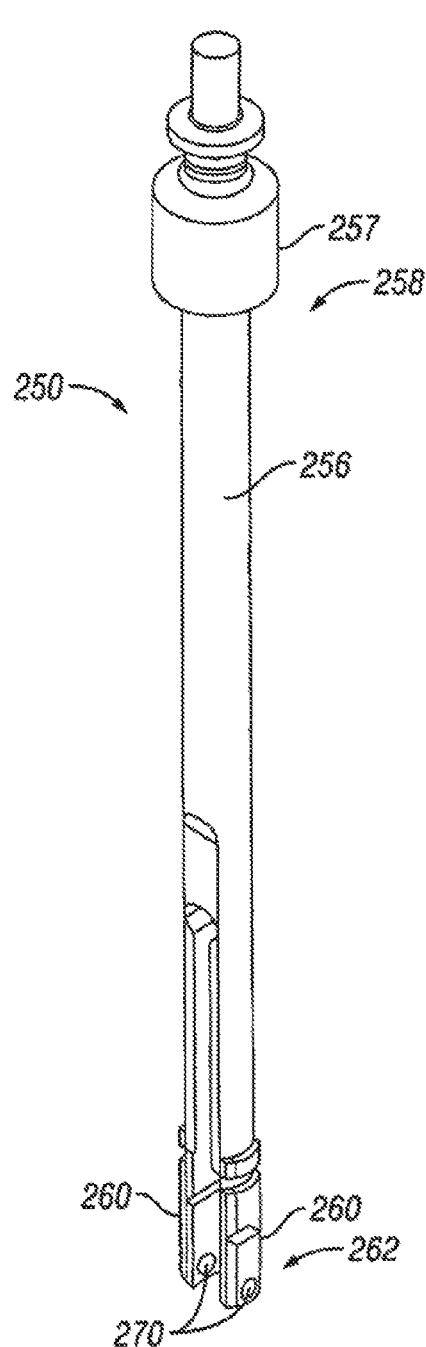
FIG. 24 is a perspective view of the forked assembly of insertion device of FIG. 21.
Figure 25:
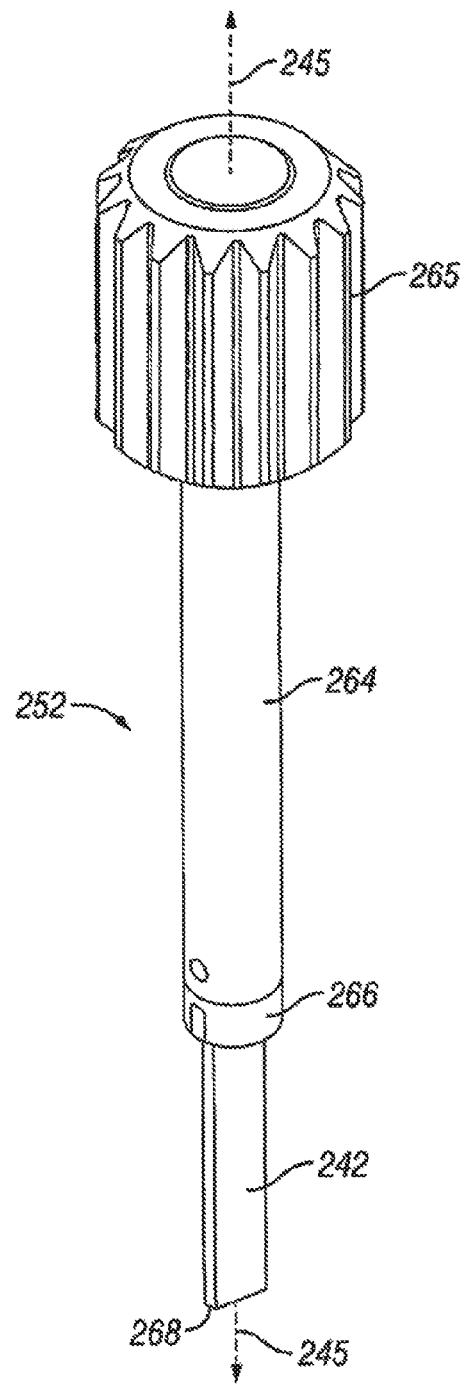
FIGS. 25-26 are perspective and cross-sectional views of the pusher assembly of FIG. 21.
Figure 28:
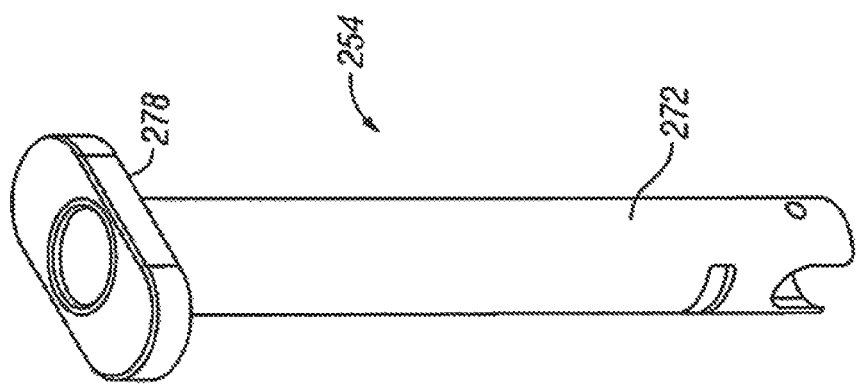
FIG. 28 is a perspective view of the retainer tube assembly of FIG. 21.
Figure 27:
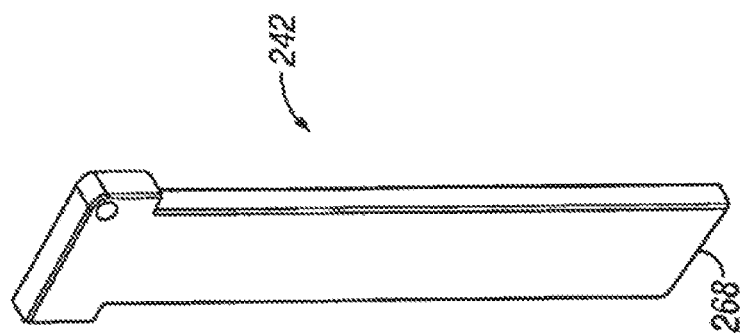
FIG. 27 is a perspective view of the pusher member of FIGS. 25-26.
Figure 26:
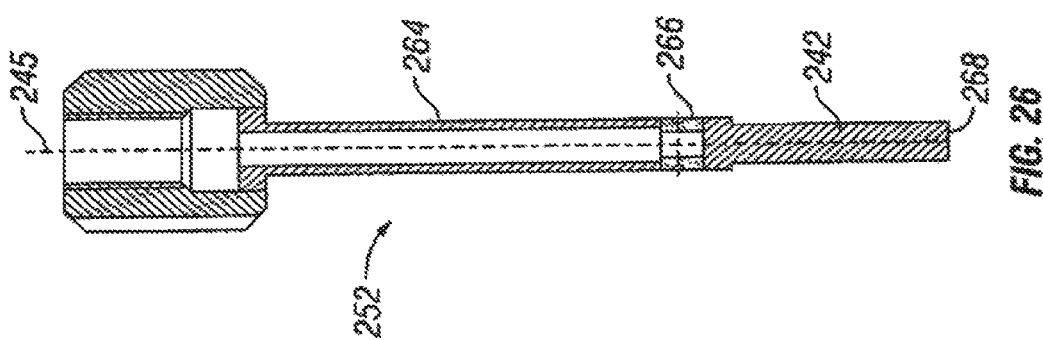
Figures 29, 30:
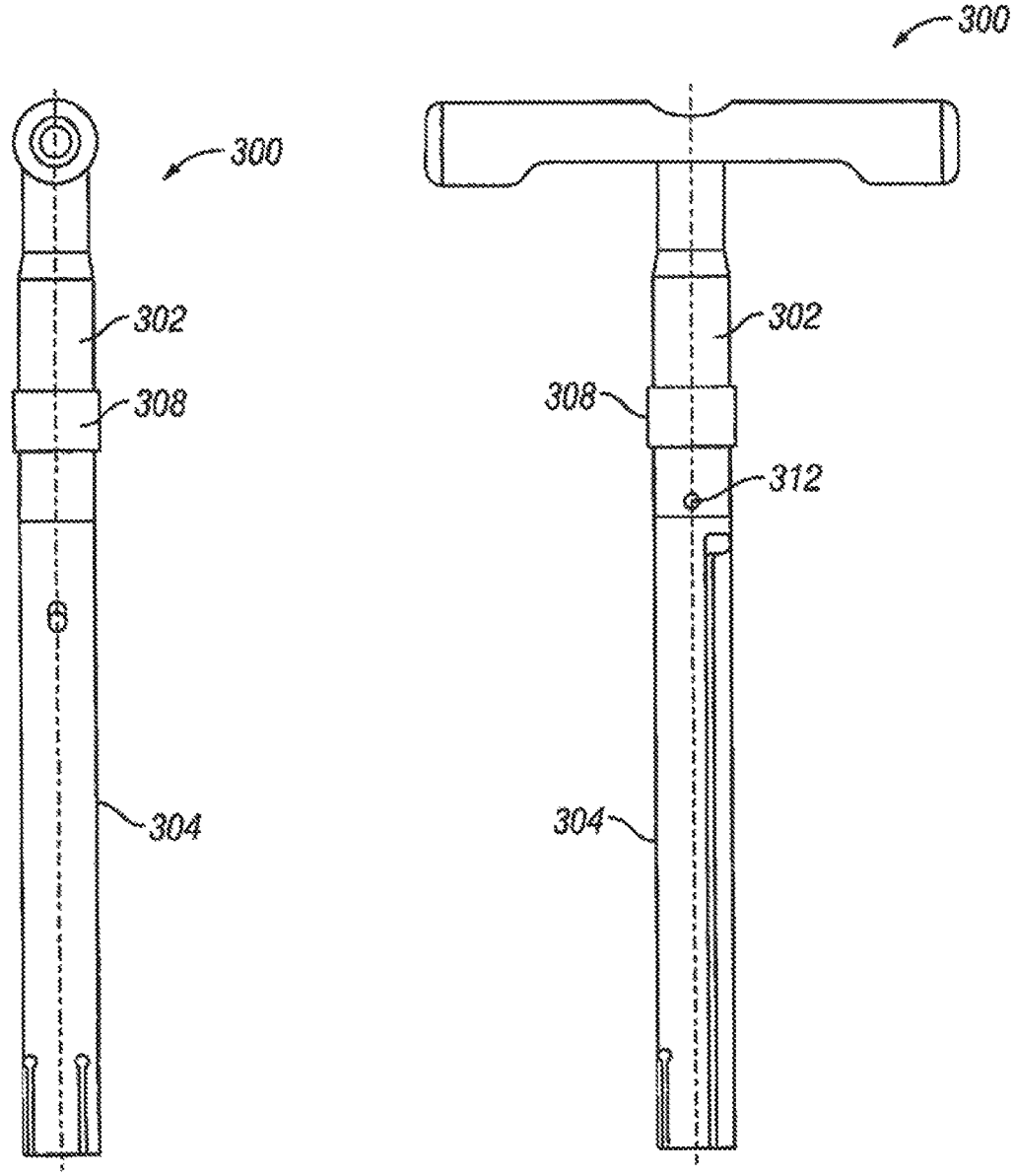
FIGS. 29-30 are side views of a rod reducer assembly according to the present invention.

Referring again to FIG. 21, stabilization member insertion device 230 is similar to insertion device 30 except rod 232 is not positively linked at its proximal end 234 to a driving link arm as described above with respect to proximal end 102 of rod 100. Insertion device 230 generally comprises a forked assembly 250, a pusher assembly 252, and a retainer tube assembly 254. As best seen in FIG. 24, forked assembly 250 generally comprises an elongate shaft 256 at a proximal end 258 and a pair of prongs or fork tines 260 at a distal end 262. As best seen in FIGS. 25-27, pusher assembly 252 generally comprises a pusher member 242 linkingly connected to a hollow turning shaft 264 by a slider 266. Slider 266 is freely rotatably connected to turning shaft 264 at its distal end such that rotation of shaft 264 causes translation of slider 266 in the distal direction along axis 245. Device 230 is similar to device 30 except driving link arm 136 of device 30 is replaced with a pusher member 242 that includes a distal end 268 configured and dimensioned to pushingly and/or slidingly engage proximal end 234 of rod 232. The pair of forked tines 260 extends distally from forked assembly 250 and are releasably linked to rod 232 by ball engaging detents 270 at pivot axis 246. In this regard, tines 260 are resiliently and outwardly expandable such that rod 232 may be inserted between detents 270 positioned adjacent the distal end of fork assembly 250.

Forked assembly 250 is dimensioned to be cooperatively received within hollow turning shaft 264 such that tines 260 extend on either side of pusher member 242. A threaded section 257 of forked assembly 250 is configured to interface with internal threads of knob 265. Retainer tube assembly 254 generally comprises a cylindrical tube 272 with a longitudinal slot 274 configured to engage a pin 276 of sleeves 22, 24, to ensure proper angular alignment with respect to sleeves 22, 24. A handle 278 may be provided to facilitate insertion of tube 272 into sleeves 22, 24, and to provide a longitudinal or axial stop to ensure that tube 272 extends a sufficient length into sleeves 22, 24, such that rod 232 may be positioned sufficiently proximate to anchors 12, 14 attached to the distal ends of sleeves 22, 24.

In operation, when knob 265 is rotated, turning shaft 264 is rotated with respect to forked assembly 250 and slider 266 is moved downward or in the distal direction along axis 245 and pusher member 242 pushes or drives the proximal end 234 of rod 232 downward or in the distal direction and causes rod 232 to rotate or pivot about pivot axis 246. Thus, rod 232 is moveable from a generally upright orientation or position or a position wherein axis 245 is aligned with axis 247 to a more horizontal orientation or position or a position wherein axis 245 is perpendicular or angled with respect to axis 247. As described above, in one embodiment stabilization member 16 is rotatably actuatable by insertion device 230 independent of movement along the axis of the sleeve, i.e. the stabilization member 16 may be rotated by insertion device 230 anywhere along the length of the sleeves 22, 24.

In general, insertion device 30 and 230 are similar in that each device generally comprises a first member and a second member, wherein the first member is linearly translatable with respect to the second member along the longitudinal axis of the device and the stabilization member is linkingly engaged to the first member and rotatably engaged to the second member. When the first member is translated with respect to the second member along the longitudinal axis, the stabilization member rotates about the second member.

Figure 13:
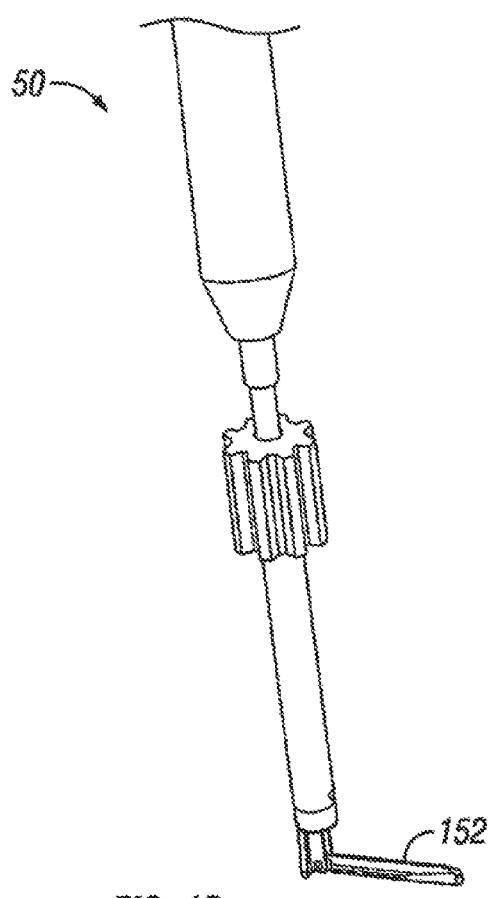
FIG. 13 is a perspective view of one embodiment of a distractor device according to the present invention.
Figure 14:
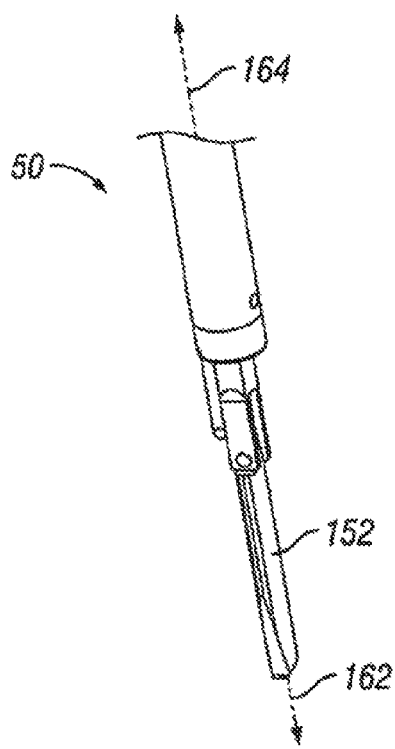
FIG. 14 is an enlarged partial perspective view of the distractor device of FIG. 13 shown in a first position.
Figure 15:
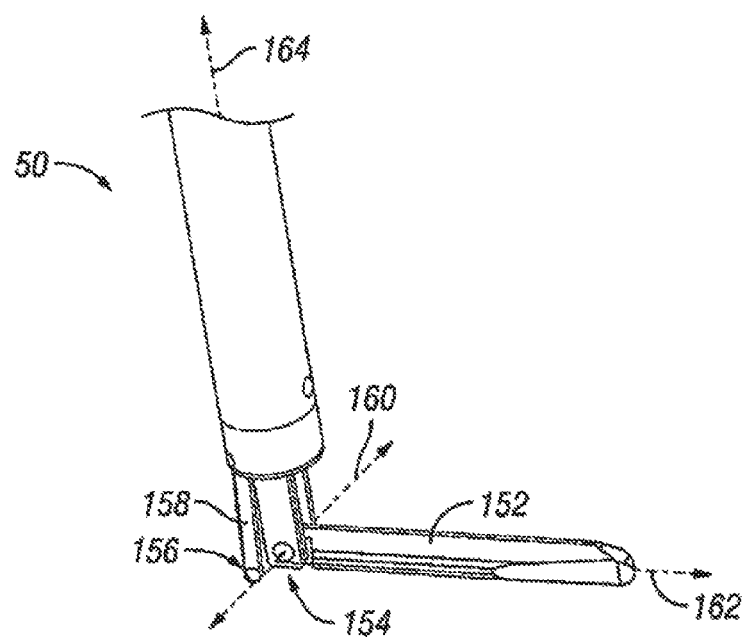
FIG. 15 is an enlarged partial perspective view of the distractor device of FIG. 13 shown in a second position.

Referring now to FIGS. 13-15, one embodiment of a distractor tool 150 according to the invention is shown. Distractor tool 150 operates similarly to insertion device 30 described above except that it has a generally straight distractor bar 152 linkedly attached to its distal end 154. The proximal end 156 of distractor bar 152 is rotatably linked to the distal end of a push rod 158 that rotates distractor bar 152 about axis 160. In operation, when push rod 158 is moved downward or in the distal direction along axis 162 push rod 158 pushes or drives the proximal end 156 of distractor bar 152 downward or in the distal direction and causes distractor bar sleeve 50 or 170152 to rotate about axis 160. Thus, distractor bar 152 is moveable from a generally upright position or a position wherein axis 162 is aligned with axis 164 (FIG. 14) to a more horizontal position or a position wherein axis 162 is perpendicular to axis 164 (FIG. 15). Distractor tool 150 is configured and dimensioned to be received within sleeve 50 or 170 and may be utilized to distract or move tissue positioned between first and second anchors 12, 14. In this regard, distractor tool 150 may be used by a surgeon to clear a pathway in the body of a patient so that stabilization member 16 may be subsequently more easily inserted. According to one aspect of the present invention, distractor bar 152 has an angled tip and a generally straight blade-like shape to facilitate tissue separation.

Figure 33:
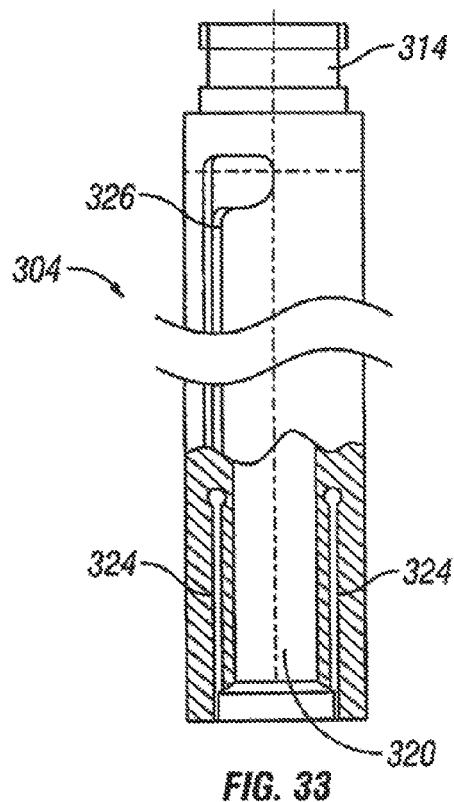
FIG. 33 is partial cross-sectional view of a reducer shaft of the assembly of FIGS. 29-30.
Figure 34:
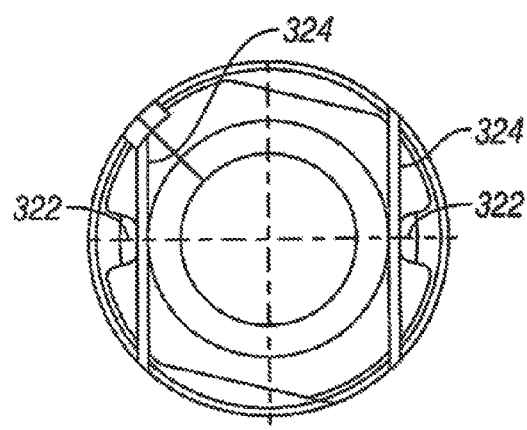
FIG. 34 is an end view of the shaft of FIG. 33.
Figure 35:
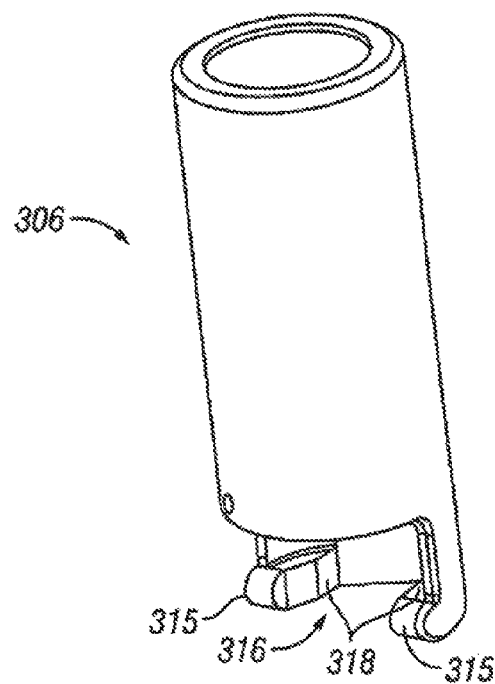
FIG. 35 is a perspective view of an attachment sleeve for use with the assembly of FIGS. 29-30.

Referring now to FIGS. 29-35, one embodiment of a rod reducer instrument 300 is shown that is configured and dimensioned to be utilized with the percutaneous systems described herein. Rod reducer instrument 300 generally comprises a rotation shaft 302, a reducer shaft 304, and an attachment sleeve 306 configured to engage and attach to a proximal end of sleeves 22, 24. Rotation shaft 302 comprises a through-hole 310 adjacent a distal end of shaft 302 and is configured to receive a pin 312 therethrough to axially connect rotation shaft 302 to reducer shaft 304. Pin 312 is configured to engage a radial slot 314 of shaft 304 such that shaft 304 may rotate freely while remaining axially fixed to shaft 302. Rotation shaft 302 comprises an externally threaded section 308 along a portion of the shaft configured to threadedly engage or mate with corresponding internal threads along the interior of attachment sleeve 306. Referring to FIG. 35, attachment sleeve 306 generally comprises a distal end having arms 315 adjacent the distal end defining a lateral opening 316 configured and dimensioned to engage and attach to the proximal end 205 of sleeves 22, 24. In this regard, arms 315 may comprise parallel flat surfaces 318 on the inner surface thereof to engage, register, and/or align with openings 220 of sleeves 22, 24 to maintain the attachment sleeve 306 in a fixed position with respect to a sleeve 22, 24 attached thereto.

Figure 31:
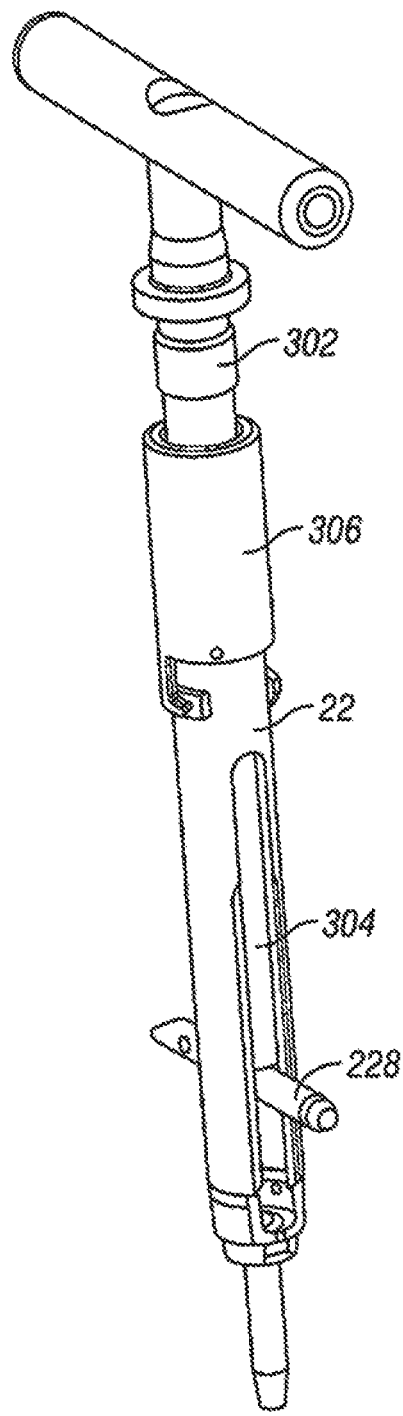
FIG. 31 is a perspective view of the assembly of FIGS. 29-30 shown in operation in a first position.
Figure 32:
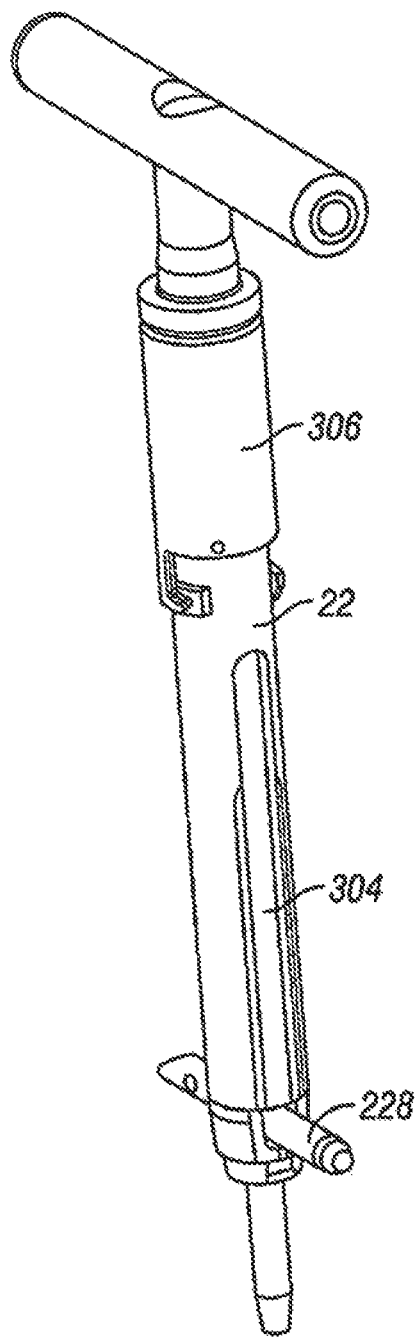
FIG. 32 is a perspective view of the assembly of FIGS. 29-30 shown in operation in a second position.

As best seen in FIG. 33, reducer shaft 304 is a cannulated shaft including a central lumen 320 extending therethrough. Radial indentation or slot 314 is provided adjacent the proximal end to axially connect with rotation shaft 302. The proximal end of shaft 304 includes a rotation tool engaging feature to facilitate rotation of shaft 304 and the distal end of shaft 304 is configured to hold a cap. Referring to FIG. 34, in one embodiment, the distal end comprises cap engaging or holding protrusions 322 extending inward to engage a cap. Furthermore, a pair of slits 324 may be provided to allow slight movement of the distal end of shaft 304 to releasably engage the fastener cap. A key slot 326 may be provided to facilitate entry and alignment with sleeves 22, 24 and by extension anchors 12, 14 attached at the distal end thereof. The cap held in the distal end has a channel or trough to engage the rod to push the rod downward toward the fastener. Referring to FIGS. 31 and 32, in operation, as shaft 302 is threadedly rotated with respect to attachment sleeve 306, reducer shaft 304 is translated in the axial direction and yet does not rotate, providing a force in the axial direction that may be used, for example, to force a spinal rod from a first position spaced from a fastener (FIG. 31) to a second position proximate to a fastener at the distal end of sleeves 22, 24 (FIG. 32). Once in place, the reducer shaft 304 can be rotated to click and/or install the cap into each fastener. In one embodiment a hex driver may be inserted through cannulated rotation shaft 302 to engage the proximal end of reducer shaft 304 to rotate reducer shaft 304 and to rotate the cap with respect to the fastener to install the cap into the proximal end of the fastener. Once the cap is installed another driving tool may be inserted through rotation shaft 302 and lumen 320 of shaft 304 to rotationally engage a set screw and the set screw can then be tightened to secure the rod in place. The rod reducer instrument 300 can then be removed from sleeves 22, 24, leaving the stabilization member 16 installed in the anchors 12, 14.

Figure 16:
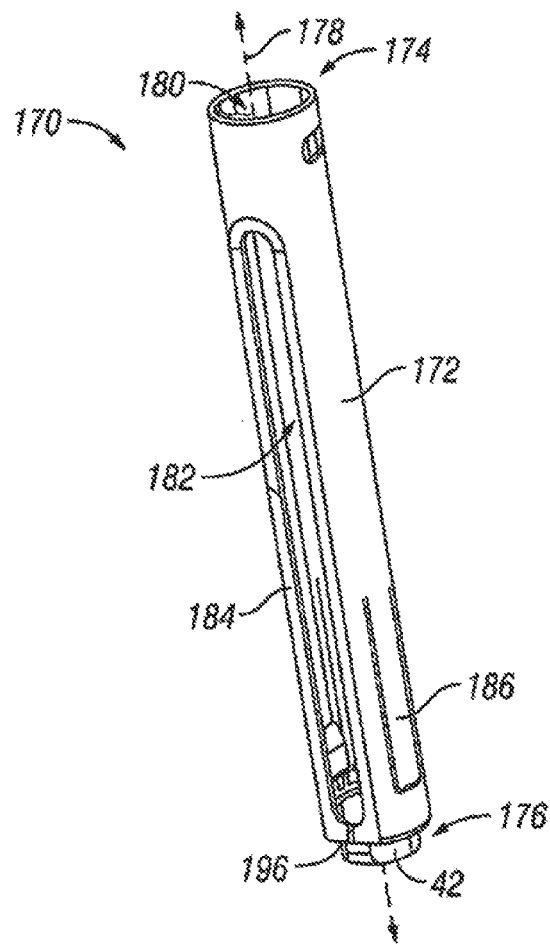
FIG. 16 is another embodiment of a sleeve according to the present invention shown engaging a portion of the anchor of FIG. 2.
Figure 17:
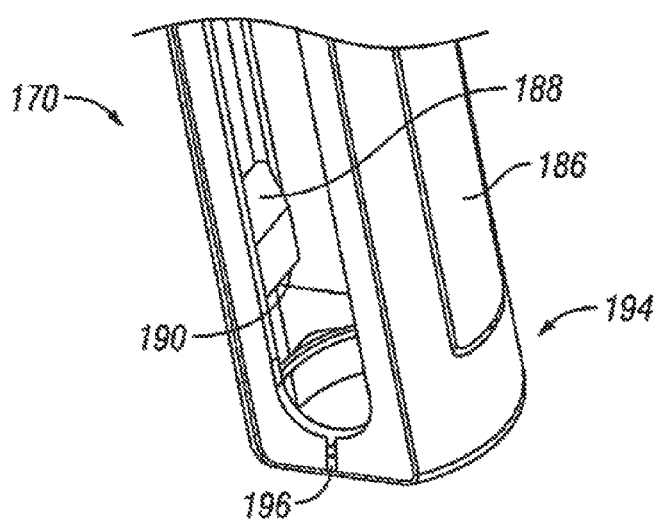
FIG. 17 is an enlarged partial perspective view of the sleeve of FIG. 16.

Referring to FIGS. 16-17, an alternative embodiment of a sleeve 170 according to the present invention is shown. Sleeve 170 generally comprises a unitary sleeve body 172 extending from a proximal end 174 to a distal end 176 along a longitudinal axis 178. A central channel 180 extends axially through sleeve body 172 and a pair of longitudinal slots or openings 182 extend through the sleeve sidewall 184 along diametrically opposite lateral sides of sleeve body 172 and provide access to central channel 180. Central channel 180 may have any desired cross-sectional shape when viewed in an end view. In one embodiment, central channel 180 is sized and dimensioned to permit a screw cap (not shown) to be inserted therein. In a preferred embodiment, channel 180 is sized and dimensioned to receive a screw therein such that the screw may be inserted from the top or proximal end 174 of sleeve 170. Sleeve 170 may also include one or more resilient tabs 186 integral with the sidewall 184. Tabs 186 include a radially inward protruding ramp portion 188 and a lip portion 190. When a screw, such as screw 32 depicted in FIG. 2, is inserted from the proximal end 174 of sleeve 170 and slid axially toward the distal end 176, the coupling element 42 of screw 32 engages ramp portion 188 to push out or radially expand tabs 186 and allow screw 32 to move distally beyond lip portion 190. Once screw 32 is in a position distally beyond lip portion 190, tabs 186 resiliently spring back radially inward such that lip portion 190 prevents coupling element 42 from moving upward or in the proximal direction.

Sleeve 170 has a retention portion 194 at its distal end that is similar to the embodiment of FIGS. 3-6 described above, except in this embodiment screw 32 is contemplated to be top loaded or inserted into the proximal end 174 of sleeve 170. Another feature of the present embodiment is sleeve 170 includes a breakable or separatable connection at its distal end. In this regard, sleeve 170 may include a break line or cut 196 to facilitate controlled breakage of sleeve 170 at its distal end 176. Sleeve 170 may be made of any material suitable for surgical instruments. In one preferred embodiment, sleeve 170 may be made from a plastic material.

Surgical techniques or methods using the above described system and device will now be described. According to one embodiment of the present invention, anchors 12, 14 may be implanted into the vertebrae percutaneously. In one preferred embodiment, each of the anchors 12, 14 is attached to, mounted on, or retained in sleeve 50 or 170, and the sleeve 50 or 170 and attached anchor are inserted through an open incision, a tube or cannula, or directly through the skin and tissue of the patient to implant anchors 12, 14 in bone, such as the pedicles of a vertebrae, as shown in FIG. 1. In alternate embodiments, anchors 12, 14 can be implanted into bone without a sleeve 50 or 170 attached thereto, and sleeve 50 or 170 may be mounted on an anchor after it is implanted.

The methods of the present invention can employ any imaging system known to those skilled in the art to determine and locate optimum placement and orientation of the anchors in the vertebrae and/or to identify locations for percutaneous skin puncture for entry of the anchors. Other methods known by skilled artisans for locating and placing anchors 12, 14 into the vertebrae may be also used, including, but not limited to, a CT scan or x-ray, any known viewing instrument or apparatus, endoscopic, and microscopic monitoring.

In one embodiment, after location of the pedicle entrance point, the percutaneous instrumentation of the pedicle may begin with the insertion of a cannulated needle through the skin of a patient to the intersection of the facet and transverse process of a vertebral body to which an anchor is to be implanted. A Kirschner wire or guidewire may be inserted through the needle cannula and into the pedicle. Successive dilation cannulas may be subsequently inserted over the guidewire to dilate the fascia and muscle until a working cannula is large enough to accommodate anchor 12 or 14. All but the largest cannula may be removed from the working cannula to expose a passageway though the skin to the pedicle or insertion site. In one embodiment, a hole in the pedicle may be prepared by placing a cannulated drill and/or tap over the guidewire and through the working cannula to prepare the pedicle for screw insertion. In other embodiments, the pedicle may be prepared with other instruments known in the art, including but not limited to an awl, a trocar, and a needle.

Once the pedicle is prepared, a cannulated anchor, such as screw 32 attached to sleeve 50 or 170, may be paced over the guidewire and advanced through the working cannula to the prepared hole. A driving tool such as a cannulated screw driver may be used to rotate screw 32 and threadedly engage screw 32 to the bone. Sleeves 50 or 170 follows screw 32 toward the bone as screw 32 is driven therein and the screw driver and guidewire may be removed. The working cannula may also subsequently be removed, leaving the sleeve 50 or 170 and screw 32 secured to the bone.

With the anchors 12, 14 secured to the bone and sleeve 50 or 170 extending therefrom, the coupling element 42 of anchors 12, 14 and the slots or openings 76 of each sleeve may be oriented or aligned. In one embodiment an alignment tool (not shown) may be attached to the proximal ends of the sleeves to ensure proper alignment of corresponding slots 76 of the sleeves 22, 24 and the channels 26 of the coupling element 42 of each anchor 12, 14.

Stabilization member 16 is positioned on insertion device 30 and readied for insertion into the channels 26 of anchors 12 and 14, respectively. Insertion device 30 may be inserted into sleeve 22 with the stabilization member 16 initially in a generally vertical position (as shown in FIG. 10). As insertion device 30 is advanced in the distal direction within sleeve 22 and shaft 142 is moved in the distal direction, rod 100 rotates or pivots about pivot axis 126 to a more horizontal position (as shown in FIG. 11). In this regard, insertion device 30 moves stabilization member 16 in a distal direction toward anchors 12, 14. The proximal end of rod 100 swings outward through opening 76 of sleeve 22 and the distal tip 108 of stabilization member 16 is advanced toward the aligned channels 26 of anchors 12, 14. In one preferred embodiment, as the insertion device 30 is advanced distally into sleeve 22 and shaft 142 is advanced distally with respect to the outer body 140 of insertion device 30, the tip 108 of stabilization member 16 follows a generally elliptical path entering the patient through first opening 18 and traveling toward the second anchor 14 and through the channel 26 of the second anchor. With rod 100 in a more horizontal position, rod 100 may be then inserted into the channel 26 of the first anchor 12 by advancing the rod insertion tool 30 distally toward the distal end of sleeve 22.

Once stabilization member 16 is placed within channels 26 of anchors 12, 14 to the desired position, a cap and/or set screw may be driven downward through sleeve 24 to contact stabilization member 16 and fix stabilization member 16 to anchor 14. A driving tool may be placed through the central channel of sleeve 24 to tighten the cap and/or set screw against the stabilization member until the stabilization member is firmly seated in coupling element 42 of anchor 14. With the stabilization member 16 fixed to anchor 14, insertion device 30 can then be uncoupled from stabilization member 16 and removed from sleeve 22 and a cap may be inserted through sleeve 22 in a similar fashion to fix stabilization member 16 to anchor 12. For sleeve 50, the outer sleeve member 54 may be retracted such that inner sleeve member 52 is in an extended condition (as shown in FIG. 3) such that arms 72, 74 of the inner sleeve member may be expanded outward to be removed around the installed stabilization member 16. In an alternate embodiment, when sleeve 170 is used, the distal end 176 is broken along break line or cut 196 to allow the distal end 176 of sleeve 170 to be removed around the installed stabilization member 16.

While the invention herein disclosed has been described with reference to specific embodiments and applications thereof, numerous modifications and variations can be made thereto by those skilled in the art without departing from the scope of the invention as set forth in the claims.

What is claimed is:

1. A method for inserting a vertebral stabilization member percutaneously, comprising:
attaching a first sleeve having a sleeve sidewall to a first bone anchor;
attaching a second sleeve having a sleeve sidewall to a second bone anchor;
coupling a rod member to an insertion device, the rod member extending from a proximal end to a distal end along a rod axis, the insertion device extending from a proximal end to a distal end along a longitudinal axis, the insertion device comprising a first member and a second member, wherein the first member is linearly translatable, the rod member is linkingly engaged to the first member at a first axial location along the rod member and rotatably engaged to the second member at a second axial location along the rod member that is axially offset from the first axial location;
inserting the insertion device into the first or second sleeve; and
pivoting the rod member from a first orientation substantially parallel to the longitudinal axis of the insertion device to a second orientation substantially perpendicular to the longitudinal axis of the insertion device such that the rod member is positioned between the first and second bone anchors,
wherein the rod member has a pair of indentations coaxially aligned on an axis that extends generally perpendicular to the rod axis and generally defines an axis about which the rod member may pivot.

2. The method of claim 1, wherein at least one of the first and second sleeves includes a pair of longitudinal slots that extend through the sleeve sidewall along diametrically opposite lateral sides of the first or second sleeve.

3. The method of claim 1, wherein at least one of the first and second sleeves includes one or more resilient tabs integral with the sleeve sidewall of at least one of the first and second sleeves.

4. The method of claim 3, wherein one or more of the resilient tabs includes a ramp portion and a lip portion.

5. The method of claim 1 further comprising, before attaching the first and second sleeves, positioning the first bone anchor in a first vertebra and positioning the second bone anchor in a second vertebra.

6. The method of claim 1, wherein the insertion device and the rod member are movable within the first or second sleeve along the longitudinal axis.

7. The method of claim 1, wherein the rod member has a curvilinear shape.

8. The method of claim 1, wherein the indentations comprise semispherical concave shapes that cooperatively engage semispherical protrusions of the first member of the insertion device.

9. The method of claim 8, wherein the first member comprises forked arm portions that may be resiliently expanded to allow the protrusions to snap into the indentations.

10. The method of claim 1, wherein indentations are semi-circular, rectangular, or triangular in shape.

11. The method of claim 1 further comprising inserting the insertion device percutaneously into a patient.

12. The method of claim 11, wherein the insertion device is operable to place the rod member through a small opening in the skin of a patient in the first orientation.

13. A method for inserting a vertebral stabilization member percutaneously, comprising:
    inserting a first bone anchor into a first vertebral body with a first sleeve connected to the first anchor;
    inserting a second bone anchor into a second vertebral body with a second sleeve connected to the second anchor;
    coupling a rod member to an insertion device, the rod member extending from a proximal end to a distal end along a rod axis and having at least one indentation along its length, the insertion device extending from a proximal end to a distal end along a longitudinal axis, the insertion device comprising a first member and a second member, wherein the first member is linearly translatable, the rod member is linkingly engaged to the first member at a first axial location along the rod member and rotatably linked to the second member about the indentation at a second axial location along the rod member that is axially offset from the first axial location;
    inserting the insertion device into the first or second sleeve; and
    pivoting the rod member from a first orientation substantially parallel to the longitudinal axis of the insertion device to a second orientation substantially perpendicular to the longitudinal axis of the insertion device such that the rod member is positioned between the first and second bone anchors.

14. The method of claim 13, wherein the indentation has a spherical shape and wherein the second member has a prong which engages the indentation.

15. The method of claim 13, wherein the rod member has a forked end, and wherein the insertion device is rotatably linked to the rod member about the forked end.

16. A method of percutaneously installing a vertebral stabilization system comprising the steps of:
    creating first and second openings in a body of a patient;
    positioning a first anchor into a first vertebral body through the first opening with a first access sleeve connected to the first anchor, the first access sleeve having a sleeve sidewall with a longitudinal slot that extends through the sleeve sidewall;
    positioning a second anchor into a second vertebral body through the second opening with a second access sleeve connected to the second anchor, the second access sleeve having a sleeve sidewall with a longitudinal slot that extends through the sleeve sidewall;
    positioning the rod member through the first or second access sleeve in a first orientation substantially parallel to a longitudinal axis of the first access sleeve; and
    rotating the rod member with respect to the insertion device independent of movement along the longitudinal axis such that the rod member extends through the longitudinal slot in the sleeve sidewall, and the rod member extends in a second orientation angled with respect to the first orientation to position the rod member between the first and second anchors,
    wherein the rod member has a pair of indentations coaxially aligned on an axis that extends generally perpendicular to the rod axis and generally defines an axis about which the rod member may pivot.

17. The method of claim 16, wherein the rod member is locked within the first and second anchors with first and second locking caps, respectively.

18. The method of claim 16, further comprising the step of removing the first and second access sleeves.

* * * * *